US008834907B2

(12) United States Patent
Lagaron Cabello et al.

(10) Patent No.: US 8,834,907 B2
(45) Date of Patent: Sep. 16, 2014

(54) ACTIVE NANOCOMPOSITE MATERIALS AND PRODUCTION METHOD THEREOF

(75) Inventors: Jose Maria Lagaron Cabello, Valencia (ES); Maria Antonieta Busolo Pons, Valencia (ES); Maria Eugenia Nunez Calzado, Valencia (ES)

(73) Assignee: Nanobiomatters, S.L., Valencia (ES)

( * ) Notice: Subject to any disclaimer, the term of this patent is extended or adjusted under 35 U.S.C. 154(b) by 480 days.

(21) Appl. No.: 13/000,797

(22) PCT Filed: Jun. 25, 2009

(86) PCT No.: PCT/IB2009/053929
§ 371 (c)(1),
(2), (4) Date: Feb. 7, 2011

(87) PCT Pub. No.: WO2009/156975
PCT Pub. Date: Dec. 30, 2009

(65) Prior Publication Data
US 2011/0142899 A1    Jun. 16, 2011

(30) Foreign Application Priority Data

Jun. 25, 2008  (ES) .................................. 200801902
Jun. 24, 2009  (ES) .................................. 200930353

(51) Int. Cl.
| | | |
|---|---|---|
| A01N 25/00 | (2006.01) | |
| C09K 15/00 | (2006.01) | |
| A01N 31/08 | (2006.01) | |
| A61K 31/05 | (2006.01) | |
| C09C 1/42 | (2006.01) | |
| B82Y 30/00 | (2011.01) | |
| C08J 5/00 | (2006.01) | |

(52) U.S. Cl.
CPC ............. *C08J 5/005* (2013.01); *C01P 2004/04* (2013.01); *C09C 1/42* (2013.01); *B82Y 30/00* (2013.01); *C08J 2300/16* (2013.01); *C01P 2002/72* (2013.01); *C01P 2004/62* (2013.01); *C01P 2004/61* (2013.01)

USPC .......................... 424/405; 252/397; 514/733

(58) Field of Classification Search
USPC .......................... 424/405; 252/397; 514/733
See application file for complete search history.

(56) References Cited

U.S. PATENT DOCUMENTS

| | | | |
|---|---|---|---|
| 6,410,142 B1 * | 6/2002 | Chen et al. ..................... | 428/402 |
| 6,410,633 B1 | 6/2002 | Hikata et al. | |
| 2007/0142534 A1 * | 6/2007 | Moad et al. .................... | 524/445 |

FOREIGN PATENT DOCUMENTS

| | | | |
|---|---|---|---|
| CA | 2635373 | * | 7/2007 |
| ES | 2277563 | | 7/2007 |

OTHER PUBLICATIONS

Zhao et al. Current Applied Physics, 7S1, 2007, e58-e62.*
Filip et al. (Food Chemistry, 83 (4), 2003, 585-593).*
Abdelwand et al. Use of and Adsorbent and Antioxidants to reduce the effects of leached phenolics in in vitro plantlet regeneration of faba bean, African Journal of Biotechnology, 2008, 7 (8), 997-1002.*
International Search Report dated Nov. 10, 2009 in re PCT/IB2009/053929, filed on Jun. 25, 2009.
Ning-Lin Zhou et la., "A New Nanocomposite Biomedical Material of Polymer/Clay-Cts-Ag Nanocomposites," Current Applied Physics Abril, 2007, vol. 7 S1, pp. e58-e62.
Xiaoying Wang et al., "Chitosan/Organic Rectorite Nanocomposite Films: Structure, Characteristic and Drug Delivery Behavior," Carbohydrate Polymers, May 1, 2007, vol. 69, pp. 41-49.
Jong-Whan Rhim et al., "Tensile, Water Vapor Barrier and Antimicrobial Properties of PLA/Nanoclay Composite Films," LTW-Food Science and Technology Marzo, 2009, Mar. 26, 2008, vol. 42, pp. 612-617.

* cited by examiner

*Primary Examiner* — Gina C Justice
*Assistant Examiner* — Genevieve S Alley
(74) *Attorney, Agent, or Firm* — Gardner Groff Greenwald & Villenueva, P.C.

(57) ABSTRACT

The present invention refers to new active nanocomposite materials, comprising a matrix and additives. The present invention also describes a process for obtaining these nanocomposite materials and their use in various industry sectors.

21 Claims, 10 Drawing Sheets

ACTIVE NANOCOMPOSITE MATERIALS AND PRODUCTION METHOD THEREOF

IN THE CROSS-REFERENCE TO RELATED APPLICATIONS

This application claims priority to Spanish Application No. P200930353, filed Jun. 24, 2009, and Spanish Application No. P200801902, filed Jun. 25, 2008, which are hereby incorporated herein by reference in their entirety for all purposes.

TECHNICAL FIELD OF THE INVENTION

The present invention refers to active and/or bioactive nanocomposite materials based on nanoclays. The activity is obtained through the formulation of a specific type of additive, based on laminates of natural and/or synthetic clays that are intercalated with metals and/or their salts, with capacity for antimicrobial activity and/or oxygen scavenging and/or with other organic, inorganic or combination of such compounds that also show antimicrobial and antioxidant properties.

The formulation of nanocomposite materials based on the incorporation of the above mentioned additives in a plastic or ceramic matrix is also described, using any manufac6868turing or processing method for plastics or for the preparation and processing of ceramic powders. Thus, the additives are incorporated into plastic matrices by methods of deposition and evaporation of solvents (e.g. coating and lamination), application of monomeric solution followed by polymerisation and curing or crosslinking or vulcanisation, operations typically used during the formulation of thermostable and elastomeric materials by melt mixing processes (e.g. extrusion, injection, blowing) and/or in situ polymerisation methods.

The nanocomposite materials with plastic matrices can be prepared by various processes typically used in the processing and manufacture of plastics such as casting techniques and/or lamination (solution and evaporation of solvent), of melt mixing, formulation of thermostable and elastomeric materials and of in-situ polymerisation, for their beneficial application both for packaging of products of interest for food and in antimicrobial plastics, in surgical equipment and also for applications in other sectors.

In the case of nanocomposite materials with ceramic matrices, these are incorporated during the preparation of powders typically used in the manufacture of ceramic products involving milling, atomisation, pressing or extrusion, enameling for enamel products, and firing.

The present invention also refers to the use of these materials for multisector applications.

BACKGROUND OF THE INVENTION

In the field of polymers, one of the areas generating a lot of interest is in the development of compound materials, more specifically of nanocomposites based on clays. There are various techniques for the preparation of nanocomposites, including the methods of casting (Ogata N, Jimenez G, Kawai H, Ogihara T; *J Polym Sci Part B: Polym Phys* 1997), melt mixing (Sinha Ray S, Yamada K, Okamoto M, Ueda K. Nano Lett 2002; 2:1093-6) and in situ polymerisation (Messersmith P B, Giannelis E P. *Chem Mater* 1993; 5:1064-6). New nanocomposites and processing techniques are also described in U.S. Pat. Nos. 5,747,560; 4,618,528; 4,528,235; 4,874,728; 6,391,449; 6,486,253; 6,376,591 and 6,156,835; WO 95/14733; WO 93/04117, and more specifically with respect to the present invention in WO2007074184A1. This PCT patent application describes a new route for manufacturing nanocomposites, which may or may not be biodegradable, with antimicrobial properties based on natural products and/or capacity for fixing or controlled release of other active or bioactive substances. These nanocomposites based on phyllosilicates and/or synthetic double layered hydroxides are intercalated with various organic modifiers. Once incorporated into thermoplastic and/or thermostable matrices, they are capable of improving barrier properties against gases and vapours. The above mentioned documents are some examples of patents and literature on polymer-clay nanocomposites prepared from modified clays. These documents describe a nanocomposite material such as an exfoliated or intercalated plate, with a tactoid structure of nanometric dimensions, which comprises intercalated clay dispersed in a polymer matrix such as an oligomer, polymer or a mixture of both.

For example, U.S. Pat. No. 4,739,007 describes the preparation of Nylon-6-clay nanocomposites from montmorillonites treated with alkyl ammonium salts by the method of melt mixing.

Protection against the action of microorganisms is a basic requirement for many current applications of plastics including preservation of the quality of packaged foods, to guarantee aseptic conditions in biomedical applications, to help reduce the growth of microorganisms on exposed and work surfaces, etc. Inventions related to the manufacture of antimicrobial systems for use in the textile, pharmaceutical and food industries have been found. More specifically, U.S. Pat. Nos. 6,841,244 and 7,232,777 describe the manufacture of silver-containing fibres with antimicrobial properties. Patents KR20030038586, U.S. Pat. No. 6,224,898 and U.S. Pat. No. 7,306,777 refer to the use of nanocomposite of metal silver and polyurethane and metal silver in dendrimeric polymers respectively, with antimicrobial properties. U.S. Pat. No. 7,306,777 and DE202005020859U describe the use of germicidal materials based on silver nanoparticles applied on packaging and packing. Patent application 200703101 comprises the manufacture of passive, (bio)active and intelligent materials and packaging with antibacterial properties by the incorporation of electrospun nanofibres containing silver nanoparticles. However, no specific design has been published to date that describes the manufacture of nanocomposites based on laminar silicates in applications for protection against the action of microorganisms.

Microorganisms, and specifically bacteria, are the main cause of diseases caused by consumption of contaminated food. They can survive the thermal treatment required for canning or even contaminate food after this treatment because of the seams or leaks from the container. In addition to the potential danger to health, proliferation of microorganisms can cause changes in foods which in turn give rise to changes in their physical, chemical and organoleptic properties. Some of the traditional preservation methods such as thermal treatments, irradiation, packaging in a modified atmosphere or by the addition of salts cannot be applied to certain types of food such as vegetables, fruits and fresh meats or ready-to-eat products. The direct application of antibacterial substances on food has limited effect because these are neutralised and diffuse rapidly towards the interior of the food. Considering the above aspects, active packaging is a viable and beneficial form of limiting and controlling bacterial growth in food as the antimicrobial agents migrate slowly from the material to the surface of the product. The migration can be as extensive as required, so that it covers the time for transport, storage and is guaranteed to consumption. In the case of antimicrobial silver nanoadditives described in the present invention, once incorporated into the packaging, they can control microbial contamination by the inactivation of the enzymatic metabolism of microorganisms.

The effect of microorganisms is also undesirable in other sectors. In the field of medicine, it is essential to remove the risks of contagion in invasive treatments, of open wounds and also in routine treatments. Examples of such treatments are coatings with antimicrobial films on catheters and stethoscopes, preparation of tissues on fibres pre-treated with silver nitrate or broad-spectrum antibiotics for treatment of wounds and burns. In the textile industry with respect to fashion or working clothing, for example, the use of fibres pre-treated with antibacterial agents limits the proliferation of microorganisms induced by sweat, humidity and elevated temperatures, reducing bad body odours and risks of contagion. The accumulation and deposition of biological material on surfaces exposed to diverse environmental conditions is known as fouling. This may occur on painted boats, objects or systems exposed to conditions of high humidity or other surfaces exposed to active, aggressive or adverse environmental conditions. In the case of boats, fuel consumption can increase by up to 50% due to hydrodynamic resistance caused by the accumulation of biological material on the hull. Antimicrobial systems can act as antifouling if applied in the form of layers on the surface of the boat, ensuring that fuel consumption is optimal and cleaning and maintenance operations are reduced in frequency. In the case of water containers and tanks, covering the interior with a film of antimicrobial compounds significantly reduces the growth of algae and the generation of bad smells, so that the quality of the water in the container is guaranteed for a longer time. Coating, or manufacturing with films of antimicrobial compounds, items such as work surfaces of laboratories (clinical, microbiological, water analysis, food), of businesses where fresh foods are handled (butchers, fishmongers, etc.), of hospital and health centre wards, to mention only a few examples, guarantees appropriate conditions of hygiene for carrying out the work and removing the risk of contamination and infections. Plastic materials with antimicrobial properties can also be used in the manufacture of cranks, handlebars, handles and armrests of public transport components, in handholds and footholds in crowded places, in the manufacture of sanitary items for mass public use, in telephone headphones and microphones and audio systems in public areas and in kitchen and food transport tools; all these applications directed at reducing the risks of propagation of infections and diseases. There is emerging interest also in manufacturing ceramic items that inhibit the proliferation of microorganisms on ceramic products, for example the proliferation of mould and mildew on surfaces covered with ceramic tiles or on the points where they join together.

In the field of ceramic materials, there are patents that describe the production of antibacterial ceramic compounds with $Ag_2WO_4$ (silver wolframate) for use on sanitary items (CN101062786); ceramic compounds with antimicrobial, fungicidal and deodorant properties containing dolomite and amphiphilic composites (JP2007169109); vitreous and ceramic materials with silver incorporated as the antimicrobial agent (US2007172661, EP1711060); antimicrobial ceramic composite of metal oxides ($Ag_2O$, $Fe_2O_3$, $MnO_2$, etc.) for preparing antimicrobial nanocomposites of low density polyethylene for use in the food industry (KR20010083418) and antimicrobial vitreous ceramic composites for odontological applications (US2005142077). The examples above show some of the applications of antimicrobial ceramic systems that remove or reduce the risk of propagation of infections and contamination in potentially infectious environments (sanitary items for public service use, for example), in environments where the control of microbial growth is essential for carrying out activities safely (for example, tiles for floors and walls of surgeries, clinical and toxicological laboratories, fish farming centres), in formulations for the preparation and/or repair of temporary or permanent dental replacement items (odontology), and in other potential applications.

Other active properties of great interest are those of "antioxidant" nature that function by sequestration of free radicals and therefore prevent oxidation processes even in the presence of oxygen, and the ability to sequester oxygen, which prevents oxidation by oxygen capture.

DESCRIPTION OF THE INVENTION

As explained above, to date there has been no description of the manufacture of nanocomposite materials that have gas and vapour barrier properties, flame retardant properties, improved mechanical and thermal properties compared to the pure polymer, with the additional ability of blocking electromagnetic radiation (UV-Visible) and allowing the fixing and/or controlled release of active and/or bioactive substances that provide, e.g. antimicrobial and/or antioxidant and/or oxygen sequestering properties. The active performance is obtained by intercalation of nanoparticles and/or of other active substances in nanoclays, which confer all of the above properties, and/or by direct addition of these to plastics and/or by addition during the formulation of nanoclays. These new materials are sufficiently thermally stable to allow manufacturing and plastic processing processes and even firing in ceramic processes.

The active properties in the present invention are conferred or reinforced by the incorporation of substances based on silver, iron or other metals and/or organic substances, either natural or synthetic, with for example biocidal, antioxidant and oxygen sequestering ability, in the structure of the nanoclays. The incorporation of metallic biocides in clays is not only interesting for the manufacture of nanocomposites based on the addition of such additives to plastics, but also because metallic biocides resist thermal treatments that may also be necessary for encouraging the reduction of salts of metal biocides to their corresponding metals and they can also be used in the ceramic industry for the manufacture of ceramic and porcelain products with antimicrobial properties. Some metals such as iron are easily oxidised and therefore can be used to sequester oxygen in applications where this gas may be a problem for product conservation. Some natural substances such as resveratrol, have antioxidant and bioactive properties, that is, in addition to their antioxidant nature, by their ability to fix free radicals and bring health benefits when they are ingested, if there is migration from the plastic.

The availability in the ceramic industry of antimicrobial nanoadditives enables the effectiveness of these products to be increased due to the high dispersion of nanoparticles in these matrices. Thus, excellent results are obtained with smaller proportions of nanoadditives, and therefore a significant reduction in costs.

The examples described above also enable the definition of the field of application of new nanocomposite materials with active properties based on metals and natural or synthetic substances. The procedure for obtaining them is revealed in the present patent. In the present invention, it was found that antimicrobial nanocomposites of metals and some ammonium salts, e.g. hexadecyltrimethylammonium bromide, allowed to have contact with food, are very powerful antimicrobial agents and therefore inhibit development, growth and proliferation of microorganisms and also propagation of infections in a wide range of applications such as packaging (food, drugs and medicines), fibres and textile fabrics, medical-surgical materials, antifouling systems and in the manufacture of plastic items for public areas and for ceramic products.

Therefore, the present invention refers to active nanocomposite materials, obtained by the introduction of laminar nanoadditives, with or without prior modification by antimicrobial quaternary ammonium salts, and/or chitosan and/or derivatives of this antimicrobial agent that have metal nanoparticles and/or their organic and inorganic salts and/or natural thermally resistant antioxidants with bioactive properties such as resveratrol intercalated in plastic or ceramic matrices, with beneficial application in sectors of coatings, medicine, construction, anti-odour textiles and packaging.

Consequently, a first essential aspect of the present invention refers to nanocomposite materials that have a plastic or ceramic matrix and are constituted by the incorporation of laminar clay nanoadditives.

Plastic matrices are selected from, without being limited to, the group formed by thermostable and elastomeric thermoplastics such as polyolefins, polyesters, polyamides, polyimides, polyketones, polyisocyanates, polysulphonates, styrene plastics, phenolic resins, amide resins, ureic resins, melamine resins, polyester resins, epoxide resins, polycarbonates, polyvinylpyrrolidones, epoxy resins, polyacrylates, rubbers and gums, polyurethanes, silicones, aramids, polybutadiene, polyisoprenes, polyacrylonitriles, PVDF, PVA, PVOH, EVOH, PVC, PVDC or derivatives of biomass and biodegradable materials such as proteins, polysaccharides, lipids and biopolyesters or mixtures of all these and can contain all types of additives typically added to plastics to improve their manufacture and/or processing or their properties. In addition, this type of matrix is in a proportion from 5% up to 99.99%; preferably from 20% to 99.99%, and more preferably from 90% to 99.99%.

Ceramic matrices comprise, but are not limited to, water, clays (preferably kaolinites and sometimes montmorillonites), deflocculates, feldspars, feldspar sands and sometimes kaolin, carbonates and zirconium. Ceramic matrices of the enamel type and other types of ceramic coatings comprise, but are not limited to, kaolin or a kaolin (5%) or montmorillonite (1%) clay, feldspars, frits, silica and silica sands. In addition, this type of matrix is in a proportion from 5% up to 99.99%; preferably from 20% to 99.99%, and more preferably from 65% to 99.99%.

According to a preferred embodiment, the plastic or ceramic matrices can contain agents that have electromagnetic radiation barrier properties or fire resistance properties or other additional active or bioactive substances in addition to nanoclays selected from the group formed by antimicrobial organic and inorganic metal salts (preferably of silver, copper, nickel or cobalt), oxygen sequestering agents such as iron and its salts, low molecular weight active or bioactive substances selected from ethanol, or ethylene, or essential oils (preferably thymol, carvacrol, linalol and mixtures), or small size antimicrobial peptides (preferably bactericides), natural or obtained by genetic modification (preferably nisins, enterocins, lacticins and lysozyme), quaternary ammonium salts, preferably those allowed for contact with food, or natural or synthetic antioxidants (preferably polyphenols such as, but not limited to, resveratrol or flavonoids, vegetable extracts such as, but not limited to, eugenol or extracts of rosemary and vitamins, preferably tocopherols and tocotrienols or ascorbic acid/vitamin C, or pharmaceutical drugs, or enzymes or bio-available calcium compounds, probiotics, marine oils, symbiotics or prebiotics (non-digestible fibre).

The benefit in the use of resveratrol, added directly to plastics, or supported or intercalated in inorganic substrates (clays or amorphous materials), over the previous generic descriptions is that this component is unique from the point of view that it is thermally stable and so can be incorporated without loss of activity in plastics processing techniques, does not significantly affect transparency or optical properties of plastics, that is, it does not significantly affect either the organoleptic properties or the product's appearance, has very strong antioxidant properties after its incorporation into plastics and additionally has bioactive properties and therefore exhibits functional properties on the organism in the case of its migration to the food and/or ingestion and is effectively incorporated into clay-type substrates. The main difference between an antioxidant such as resveratrol and an oxygen sequestering agent such as iron and iron salts is that the antioxidant captures free radicals and impedes oxidation even in the presence of oxygen and the oxygen sequestering agent captures oxygen thereby preventing oxidation. In both cases, stability is improved and useful life extended of the plastic or ceramic matrix or the product contained or in contact with these active materials.

The nanoclays are selected from the group formed by laminar silicates and/or laminar double hydroxides. These materials are selected from but are not limited to the group formed by montmorillonite clays, kaolinite, bentonite, smectite, hectorite, sepiolite, gibbsite, dicktite, nacrite, saponite, halloysite, vermiculite, mica, and/pr mixtures of these or with other phyllosilicates, with or without prior organic or inorganic surface modification. These materials are characterised in that they are introduced as laminar-type loads, with sizes in the nanometer range in at least the thickness of the particle, into plastic matrices and into ceramic matrices to form new active nanocomposites.

In plastic matrices, the active additives are in a proportion from 0.01% to 95%, preferably from 0.01% to 80% and more preferably from 0.01% to 10%.

In ceramic matrices, the active additives are in a proportion from 0.01% to 95% by weight, preferably from 0.01% to 80% and more preferably from 0.01% to 35%.

In ceramic enamel-type matrices, the active additives are in a proportion from 0.01% to 50%, preferably from 0.01% to 20% and more preferably from 0.01% to 15%.

Surface modification of the clay nanoadditives when applied allows, in addition to introducing or accentuating active activity by incorporating compatibilisers with biocidal properties, increases the compatibility between the clay and the matrix to achieve better exfoliation of the clay. This results in good morphology for improving the dispersion and surface exposure of the active substances, antimicrobial agents and/or oxygen sequestrators, which are substances based on metals such as silver, copper, nickel, cobalt, iron, zinc and/or combinations of these and/or their inorganic or organic salts, organic compounds, preferably salts allowed for food contact (that is they appear in the lists of monomers and other raw material substances that are authorised by legislation for use in the manufacture of plastic materials and objects) such as, and not limited to, hexadecyltrimethylammonium bromide (which this invention has shown to be an antimicrobial agent itself), esters of polyethylene glycol with mono-carboxylic aliphatic acids (C6-C22) and their ammonium and sodium sulphates, perfluorooctanoic acid and its ammonium salt, copolymers of N-methacryloyloxyethyl-N,N-dimethyl-N-carboxymethylammonium chloride, bis(2-hydroxyethyl)-2-hydroxypropyl-3-(dodecyloxy)methylammonium chloride and chitosan and its derivatives and combinations of these. The salts of the metals are selected from but not limited to the group formed by simple salts such as nitrate, acetate, chloride, sulphate and inorganic complexes that include water and nitrate, acetate, amino and chloride groups.

In the case of plastic materials, they present active activity and improvements in barrier properties, fire resistance and in other physical properties and enable blocking of electromagnetic radiation and also allow controlled release of these or other substances with active and/or bioactive properties compared to the pure material. In the case of ceramic materials, more effective antimicrobial properties are obtained because of the nanoparticulation of the biocidal metal.

These nanocomposite materials are prepared in the case of plastics by lamination or coating (casting of the solution) techniques, by means of the application of the monomeric solution followed by polymerisation and curing, operations that are typically used during the formulation of thermostable agents, by the above process but followed by cross-linking or vulcanisation, operations typically employed in the manufacture of elastomeric agents, by melt mixing using conventional techniques for processing of plastics from polymer or plastic pellets or by in situ polymerisation.

In the case of application in ceramics, they are incorporated during, but are not limited to, the preparation of powders typically used in the manufacture of ceramic products involving milling, atomization, pressing or extrusion, enamelling for enamel products, and firing.

Nanocomposite plastics are of particular interest in the food packaging industry, because these active packaging materials enable the protection of the product from the action of microorganisms, protection of the pack and its contents from oxidation, either by the use of antioxidants that sequester free radicals or of oxygen sequestration agents that remove oxygen, and/or fixing and/or controlled release of these or other active substances, and additionally, they notably improve the gas and vapour barrier properties, mechanical barrier properties to UV and other properties typically associated with the use of nanoclays. In other application fields, plastic and ceramic nanocomposite materials reinforced with nanoclays with active properties are useful in the medical-surgery area, biomedicine and pharmaceuticals, for the manufacture and coating of equipment and materials used in routine and invasive treatments. They are also useful in anti-fouling applications to prevent the formation of biofilms on submerged surfaces and those exposed to water and humidity, and in general, for all applications in which an item, accessory or coating is required of an antimicrobial compound and/or antioxidant or oxygen sequestrator, to prevent the proliferation of microbes and risks of infection and/or oxidation of the materials and/or the contents or products in contact with them.

A second essential aspect of the present invention refers to the process for the manufacture of the nanocomposite materials described in the present invention, which can be based on structures such as laminar phyllosilicates, including clays (e.g. montmorillonite, kaolinite, bentonite, smectite, hectorite, sepiolite, saponite, halloysite, verminculite, mica) or synthetic or natural laminar double hydroxides with laminar structure and which comprises the following stages:

1) Reduction of the size of the laminar particles by mechanical action, for example by grinding technologies. This process is carried out to obtain a d90 particle size below 30 microns.
2) Classification in a vibrotamiz, centrifuge, filter press or any other dry or wet filtration system to a range of between 0.1 to 100 microns, preferably the reduction of particle size achieved is below 25 microns and more preferably below 3 microns in the so-called d90 measure (no more than 10% of the material has a diameter above this value).
3) Alternatively, removal of organic material by, but not limited to, techniques of decantation, collection of the supernatant or by chemical reaction with oxidising substances such as peroxides.
4) Alternatively, removal of crystalline oxides and hard particles not subject to modification, either by centrifugation processes and/or gravimetric methods in solution or by turbo-dryers, preferably by a centrifugation process either in wet or in dry route, which may or may not be followed by a process of atomization with controlled depression or by any other process of industrial drying including lyophilisation.
5) Obtaining laminar fines, either in liquid suspension or by subsequent drying by the methods described in step 4) in powder. These systems, both in liquid suspension and in powder are considered as the starting product of the present invention.
6) Pre-treatment of the laminar structures in one or in several steps, by the use of expander-type precursors as shown in Table 1.

TABLE 1

| MODIFIER | $d_{MODIFIER}$ (nm) | MODIFIER | $d_{MODIFIER}$ (nm) |
|---|---|---|---|
| Unmodified Kaolinite | 0.72 | Unmodified Montmorillonite | 0.98 |
| Dimethyl sulphoxide (DMSO) | 1.11 | Ethylene polyoxide | 1.12 |
| Silver nitrate | 0.74 | Silver nitrate | 0.99 |
| Silver acetate | 0.74 | Silver acetate | 0.99 |
| Nickel chloride | 0.75 | Nickel chloride | 0.99 |
| Cobalt chloride | 0.76 | Cobalt chloride | 0.99 |
| Copper nitrate | 0.76 | Copper nitrate | 1.00 |
| Ammonium iron sulphate | 0.74 | Ammonium iron sulphate | 1.00 |
| N-methyl formamide (NMF) | 1.02 | Cellulose aceto butyrate | 1.13 |
| Hydrazine Hydrate | 1.03 | Calcium butyrate | 0.92 |
| Water | 0.78 | Sucrose Aceto Isobutyrate | 1.08 |
| Alcohols | 1.10 | Manganese butyrate | 0.95 |
| Anhydrous hydrazine | 0.96 | Carboxymethyl starch | >3 |
| Acetamide | 1.09 | Starch | 1.21 |
| DMSA + Methanol (MeOH) | 1.12 | Hydroxyethyl starch | 1.15 |
| Hexanoic acid | 1.23 | Hydroxypropyl starch | 1.14 |
| Acrylamides | 1.44 | Adonitol | 1.04 |
| Glucose | 1.25 | Sorbitol | 1.19 |
| Acrylamide | 1.14 | Dibenzylidensorbitol | 1.16 |
| Salicylic acid | 1.07 | Ethylene glycol | 0.95 |
| Manganese acetate | 1.41 | Polypropylene glycol | 1.01 |
| Caprolactam | 1.18 | Propylene glycol | 1.01 |
| Vinyl acetate | 1.21 | Glycolic acid | 1.06 |
| Potassium acetate | 1.39 | Triethylene glycol | 1.08 |
| Tannic acid | 1.09 | Tetraethylene glycol | 1.06 |
| Maleic acid | 1.20 | Glycerol | 1.02 |
| Maleic anhydride | 1.20 | 1,2-Propanediol | 1.09 |
| Lactic acid | 1.08 | 1.3-Propanediol | 0.98 |
| Adipic acid | 1.03 | Polyethylene glycol $M_w = 1000$ | 1.11 |
| Acetic acid | 1.10 | Polyethylene glycol $M_w = 3400$ | 1.12 |
| Acetaldehyde | 0.91 | Sorbitan | 1.09 |
| Butyric acid | 1.01 | Dipropylene glycol | 1.03 |
| Tetrafluoroethylene | 0.98 | Diethylene glycol | 1.04 |
| Chlorotrifluoroethylene | 1.05 | Vinylpyrrolidone | 1.23 |
| Hexamethylene | 1.02 | Vinyl versatate | 1.11 |

The expanders are preferably selected from the group formed by DMSO, alcohols, acetates, or water and a mixture of the above, and metallic salts of silver, copper, iron, nickel or cobalt, which activate the fines by an initial increase of the basal spacing of the layers and modify the surface characteristics of the clay. The penetration of the precursors is accelerated by, but not limited to, the use of temperature, turbulent homogeniser, ultrasound, supercritical fluids, deflocculating agents such as acrylates and/or phosphates, pressure or a mixture of these. Drying, following washing with water or alcohols, can be performed by evaporation in an oven, lyophilisation, centrifugation and/or gravimetric processes in solution or turbo-dryers or by atomization. According to another preferred embodiment of the present invention, the solution of the intercalated precursor can be used, without a prior washing and/or drying process, as the raw material for the following stage of incorporation of the modifier.

7) Additionally or optionally, inorganic, organic or hybrid substances can be intercalated into the laminar structure in aqueous base or with polar solvents. In this sense, the compounds to be intercalated are selected from but not limited to the group formed by PVOH, EVOH and derivatives of the same family, and/or biopolymers such as peptides and natural or synthetic proteins via chemical or genetic modification of microorganisms or plants and polypeptides, lipids, nucleic acids and polymers of synthetic nucleic acids obtained via chemical or generic modification of microorganisms or plants and biodegradable polyesters such as polylactic acid, poly (lactic/glycolic acid), polycaprolactone, adipic acid and derivatives and the polyhydroxyalcanoates, preferably polyhydroxybutyrate and its copolymers with valeriates, biomedical materials such as hydroxyapatites and phosphates of organic salts, and/or natural or synthetic antioxidants (preferably polyphenols such as, but not limited to, resveratrol or flavonoids, vegetable extracts such as, but not limited to, eugenol or extracts of rosemary and vitamins, preferably tocopherols and tocotrienols or ascorbic acid/vitamin C). It is also possible to intercalate quaternary ammonium salts, preferably salts allowed for food contact (that is they appear in the lists of monomers and other raw material substances that are authorised by legislation for use in the preparation of plastic materials and objects) such as but not limited to, hexadecyltrimethylammonium bromide, esters of polyethylene glycol with mono-carboxylic aliphatic acids (C6-C22) and their ammonium and sodium sulphates, perfluorooctanoic acid and its ammonium salt, copolymers of N-methacryloyloxyethyl-N,N-dimethyl-N-carboxymethylammonium chloride, bis(2-hydroxyethyl)-2-hydroxypropyl-3-(dodecyloxy)methylammonium chloride and chitosan and its derivatives, silver, iron, copper, nickel and/or their organic or inorganic salts and other particles or nanoparticles with antimicrobial, antioxidant or oxygen sequestration properties and/or and combinations of all the above.

When the inorganic material that is intercalated is based on metals such as silver or organic and/or inorganic salts of silver, copper, iron, cobalt, nickel or other metals with antimicrobial or oxygen sequestration properties, a physical or chemical treatment can later be applied to change the oxidation state of the intercalated metallic centre, either totally or partially. These treatments include but are not limited to: re-firing at high temperatures (250-1200° C.), UV radiation, infrared radiation, microwave radiation, chemical reduction by ethanol and/or $NaBH_4$ and/or other chemical reducing agents. After completing any of these treatments, the degree of oxidation of the metallic centre (silver, copper, iron, nickel, zinc, cobalt or another metal used) will have been modified, either totally or partially, conferring on the material antimicrobial and/or oxygen sequestration properties that are stronger or weaker.

When the organic material that is intercalated is EVOH or any material of the same family with molar content of ethylene preferably less than 48%, and more preferably less than 29%, these are brought to saturation in aqueous medium or in specific alcohol-type solvents and mixtures of alcohols and water, more preferably of water and isopropanol in proportions by volume of water greater than 50%.

The biopolymers, with or without plasticisers, with or without cross-linkers and with or without emulsifiers or surfactants or other type of nanoadditives, are of the group formed by synthetic and natural polysaccharides (vegetable or animal) such as cellulose and derivatives, carraghenates and derivatives, alginates, dextran, arabic gum and preferably chitosan and any of its derivatives, both natural and synthetic, more preferably chitosan salts and still more preferably chitosan acetate, and proteins, both derived from plants or animals and maize proteins (zein), derivatives of gluten such as gluten or its gliadin and glutenin fractions and more preferably gelatin, casein and soya proteins and derivatives, as well as natural or synthetic polypeptides, preferably of elastin type obtained via chemical or genetic modification of microorganisms or plants, lipids such as bees wax, carnauba wax, candelilla wax, shellac and fatty acids and monoglycerides and/or mixtures of all the above.

In the case of chitosan, the degree of deacetylation should preferably be higher than 80% and more preferably higher than 87%. The penetration of the precursors is accelerated by the use of temperature, a turbulent homogeniser, ultrasound, pressure or a mixture of the above.

In a subsequent step, or alternative to modification of the fines, pre-treated with the precursors and modifiers previously mentioned, that may have been washed and dried using the methods previously cited or maintained in liquid medium, low molecular weight substances may be added that are active or bioactive, the purpose of which is either to be intercalated and remain fixed or for controlled released, giving rise to composites with active or bioactive properties. The active substances may be ethanol, or ethylene, or essential oils (preferably timolol, carvacrol, linalol or mixtures of these), or small size antimicrobial peptides (preferably bactericidal), either natural or obtained by genetic modification (preferably nisins, enterocins, lacticins and lysozyme), or natural or synthetic antioxidants (preferably polyphenols such as, but not limited to, resveratrol or flavonoids, plant extracts such as, but not limited to, eugenol or extracts of rosemary and vitamins, preferably tocopherols and tocotrienes or ascorbic acid/vitamin C) or pharmaceutical drugs, or enzymes or bioavailable calcium compounds, marine oils, probiotics, symbiotics or prebiotics (non-digestible fibre), or organic and inorganic metallic salts (preferably of silver, copper, iron nickel or cobalt). It is expected that these elements can remain fixed and/or later released from the nanocomposite towards the product in a controlled way (matrix control) and exercise their active or bioactive role, and/or that they can be released from the matrix and that the nanoclays control the kinetics (nanoadditive control). The contents to be added are generally less than 80% in volume of the solution, preferably less than 12% and more preferably less than 8%. The penetration of these substances is accelerated by, but not limited to, the use of temperature, a turbulent homogeniser, ultrasound, pressure or a mixture of the above.

8) Adding the result of the previous stages in solid or liquid state to a plastic or ceramic matrix. Alternatively, active organic and inorganic metallic salts (preferably of silver, iron, cobalt, nickel or cobalt) and/or any other type of active or bioactive substances, but not limited to the above mentioned, can also be included in the matrix containing the active nanoclays and as an addition, in order to reinforce or complement the active or bioactive effect of the nanocomposite. In the case of plastic matrices, both the nanoclays and the complementary compounds mentioned above can be added during processing using any manufacturing method associated with the plastics processing industry such as extrusion, application and curing processes typically used for manufacturing and shaping thermostable and elastomeric materials, injection, blowing, compression moulding, resin transfer moulding, calandering, thermal shock, internal mixing, ultrasound, co-extrusion, co-injection and a mixture of these.

In another preferred embodiment of the present invention and alternatively for use as intercalation agent in nanoclays, there can be added directly to polymers or plastics, either via liquid dispersed in polar or apolar solvents or via solid, natural or synthetic antioxidant substances such as those previously described and more preferably resveratrol. These antioxidant substances can be processed by any plastics processing method to obtain a concentrate or can be processed by any plastics processing method for obtaining plastic articles to obtain pellets.

According to a preferred embodiment, the polymeric or plastic matrix (in this invention, the term plastic and polymer are used without distinction) can be any thermoplastic, thermostable or elastomeric plastic or derivatives of biomass and biodegradable materials such as proteins, polysaccharides, lipids and biopolyesters or mixtures of all of these and can contain any type of additive that improves the electromagnetic radiation barrier and fire resistance properties and/or other different nanoadditives typically added to plastics to improve their processing or properties. Alternatively, a precipitation by evaporation of the resultant of the combination of nanoadditives and modifiers can be carried out and also, optionally of the plastic matrix in solution, using gravimetric drying methods such as heating and/or centrifugation and/or turbo-driers and/or atomization; by cooling or by addition of a precipitation agent to form either a powder of the additive or a masterbatch or, what is the same thing, a concentrate of the nanoadditive in a plastic matrix.

In the case of the ceramic matrix, the organic and/or inorganic metallic salts with active properties can be added together with other active or bioactive substances in any of the ceramic materials manufacturing or processing stages, although preferentially they are added during the preparation of powders before atomization.

The additive concentrates in the polymeric matrix can be treated in the following ways:
a) They are crushed to give rise to a particulate product by milling.
b) They are processed by any plastic processing method to obtain solid state pellets.
c) They are processed by any manufacturing process associated with the plastics processing industry such as extrusion, injection, blowing, compression moulding, resin transfer moulding, calandering, thermal shock, internal mixing, ultrasound, co-extrusion, co-injection or a mixture of these.
d) They are used as additives on any plastic matrix (including biopolymers and biomedical materials cited) by any of the conventional plastics processing routes described above.

Finally, when the nanocomposite material is reinforced with nanoclays containing metals such as silver or organic salts and/or inorganic salts of silver, copper, cobalt, nickel or other metals with antimicrobial power, iron and/or its salts, a physical or chemical treatment can be applied, whether or not previously applied, to change, totally or partially, the oxidation state of the intercalated metallic centre in the plastic or ceramic matrix, either before, during or after shaping. These treatments include but are not limited to: re-firing at high temperatures (250-1200° C.), UV radiation, infrared radiation, microwave radiation, chemical reduction by ethanol and/or $NaBH_4$ and/or other chemical reducing agents. After completing any of these treatments, the degree of oxidation of the metallic centre (silver, copper, iron, nickel, zinc, cobalt or another metal used) will have been modified, conferring beneficial antimicrobial and/or oxygen sequestration properties on the material.

Lastly, a third essential aspect of the present invention refers to the use of the nanocomposite materials to reinforce antimicrobial activity in multisector applications in which there is a requirement to limit microbial proliferation through the use of plastic and ceramic composite materials, particularly in applications of packaging and packing in general of foods and food components (in the case of polymeric materials), in biomedical, medical-surgical and pharmaceutical applications, or in antifouling applications, in construction applications for enamel and tiling, in applications for personal hygiene products and in applications involving contact in crowded places such as supermarkets, trolleys, stands, walkways, escalators or airports, in textile applications, as a barrier to gases, vapours, solvents and organic products such as aromas and aroma components, oils, greases and hydrocarbons, and for mixed organic and inorganic products for applications requiring biodegradable or compostable materials, for active packaging that requires antimicrobial, antioxidant activity, or of other types of activity requiring controlled release of low molecular weight substances, preferably volatile materials, for applications requiring antimicrobial, antioxidant or oxygen sequestration ability and for use of biopolymers, either without the need for the use of plasticising agents or the need to use lower amounts of these.

These nanocomposite materials also serve as materials with electromagnetic radiation barrier and fire resistant properties.

All the characteristics and benefits expressed as well as others deriving from the invention can be better understood with the following examples. The examples shown below are not limiting but only illustrative in nature and are given so that the present invention can be better understood.

BRIEF DESCRIPTION OF THE FIGURES

The invention is described below with reference to the attached figures, where.

EXAMPLES

Example 1

Figure 1:
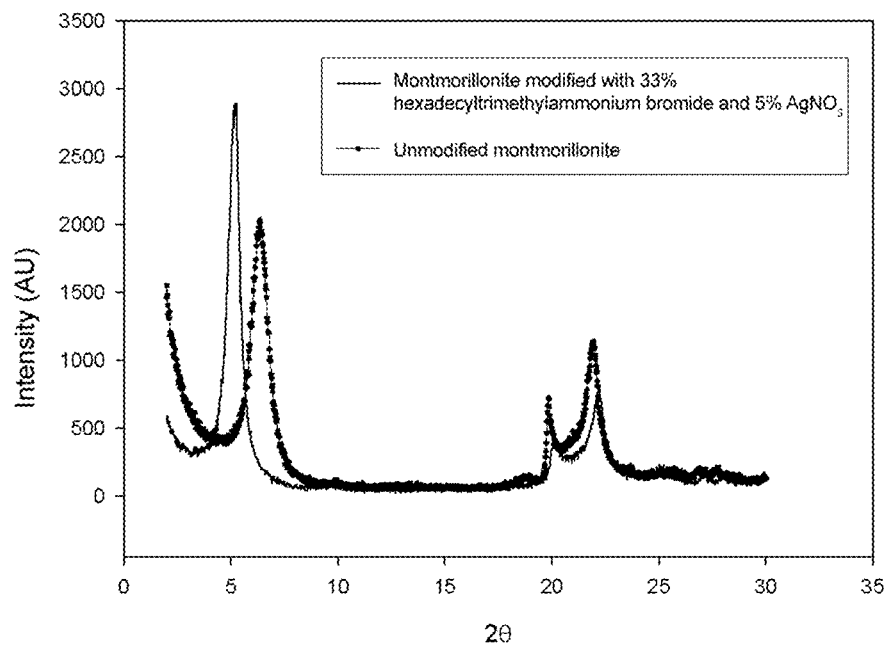
FIG. 1 shows X-ray diffractograms (WAXS) obtained from a sample of montmorillonite-type clay modified with hexadecyltrimethylammonium bromide (organic antimicrobial, expander and compatibilising agent) and silver nitrate (temperature-resistant antimicrobial), using ethanol as the reducing agent by the method described in Example 1, and a sample of the same type of clay without modification. This figure shows how the antimicrobial system is intercalated in the clay and displaces the natural peak of the clay to lower angles.
Figure 2:
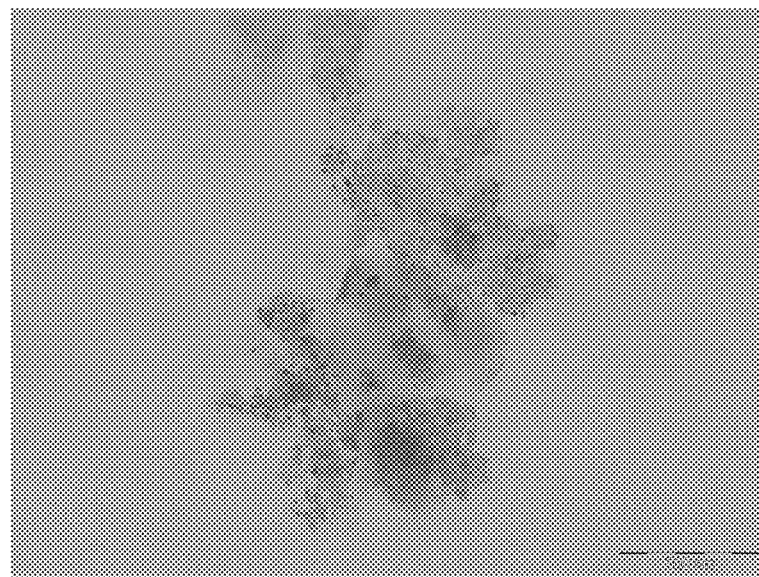
FIG. 2 is an image obtained by transmission electron microscopy (TEM) showing the main morphologies that can be seen in nanoloads obtained according to the present invention. The image corresponds to an aggregate of montmorillonite-type clay layers modified with hexadecyltrimethylammonium bromide and silver nitrate, using ethanol as the reducing agent, by the method described in Example 1. The silver nanoparticles formed on the surface can be seen.

Synthesis and Intercalation of Metallic Silver Nanoparticles in Montmorillonite-Type Clays Modified with 33% by Weight of Hexadecyltrimethylammonium Bromide, Using Ethanol as the Reducing Agent First, the clay, already modified with 33% hexadecyltrimethylammonium bromide, was dispersed in ethanol at room temperature, using 1 g of clay per 100 g solvent, and 0.05 g $AgNO_3$ added to the dispersion. The dispersion was refluxed at 70° C. for 6 hours; then the dispersion was decanted, excess solvent removed and the clay was dried in a convection oven for 1 h at 70° C. The resulting clay was characterised by X-ray diffraction (see FIG. 1) and transmission electron microscopy (see FIG. 2). The diffractograms of FIG. 1 show that the modifying agents (particles of silver and hexadecyltrimethylammonium bromide) were intercalated between the layers, according to the displacement of the basal peak at very low angles (from 6.38 to 5.26). From the TEM images, it was determined that in this case the silver nanoparticles were between 3 and 23 nm, with an average size of 16 nm; and that these nanoparticles were presumably located in the interlaminar spaces of the clay, on the surface and edges.

In another study, the antimicrobial ability of this clay with 5% silver nitrate was determined against *Salmonella* spp. A pathogenic microorganism of food origin, *Salmonella* spp. CECT 554, was used, which was obtained from the Spanish Collection of Culture Types (Valencia, Spain). The study conditions were set to use the bacteria in middle exponential phase and with an initial concentration of microorganisms of approximately $10^5$ CFU/mL. The experimental part was carried out using an adaptation of the method of macro dilution established for the determination of bactericidal activity of antimicrobial agents approved in 1999 by the National Committee for Clinical Laboratory Standards. According to this method, 100 mg of the clay, which had a final silver concentration of 5% and hexadecyltrimethylammonium bromide concentration of 33%, was placed in a sterile tube containing 10 mL culture broth Mueller Hinton Broth (MHB). After 5 hours, the tube was inoculated with 0.1 mL of a culture of *Salmonella* spp. in the condition described above. In parallel, two tubes containing a sample without silver (one with a clay of the same type but with no modification and the other with clay of the same type modified with 33% hexadecyltrimethylammonium bromide), and another tube without a sample that acted as a control, were inoculated. After the samples were inoculated, all the tubes were incubated at 37° C. for 24 hours. Next, 0.1 mL of each sample was seeded on Tryptone Soy Agar (TSA) plates. After 24 hours of incubation at 37° C., the viable cells on the plate were counted. Except for the control without a sample and the unmodified clay control, a significant reduction in the number of viable cells after incubation at 37° C. and 24 hours incubation was obtained (see Table 2). The clay modified with 33% hexadecyltrimethylammonium bromide control showed a reduction of three orders of magnitude of the number of viable cells after the incubation period, showing that this modifying agent has some antibacterial activity. The sample of clay modified with 5% of silver nitrate and 33% of hexadecyltrimethylammonium bromide reduced the number of viable cells by more than 99.9%, demonstrating the bactericidal capacity of this clay.

TABLE 2

| Sample | Initial CFU/mL | Final CFU/mL |
|---|---|---|
| Control without sample | $7.0 * 10^5$ | $3.8 * 10^9$ |
| Control of unmodified montmorillonite-type clay | $7.0 * 10^5$ | $2.0 * 10^9$ |
| Control of montmorillonite-type clay modified with 33% hexadecyltrimethylammonium bromide | $7.0 * 10^5$ | $1.4 * 10^2$ |
| Montmorillonite-type clay modified with 33% hexadecyltrimethylammonium bromide and with 5% AgNO$_3$ | $7.0 * 10^5$ | <1 |

Example 2

Synthesis and Intercalation of Metallic Silver Nanoparticles in Kaolinite-Type Clays Ore-Treated with Dimethyl Sulphoxide (DMSO) and Modified with 33% by Weight of Hexadecyltrimethylammonium Bromide, Using UV Radiation as the Reducing Agent First, the kaolinite-type clay was pre-treated with dimethyl sulphoxide to increase interlaminar spacing. For this, 60 g of clay was dispersed in 300 ml of dimethyl sulphoxide, and was stirred magnetically at 65° C. for 24 hours. Next the clay was filtered by suction, washed with methanol and dried in a convection oven at 80° C. for 6 hours.

Figure 3:
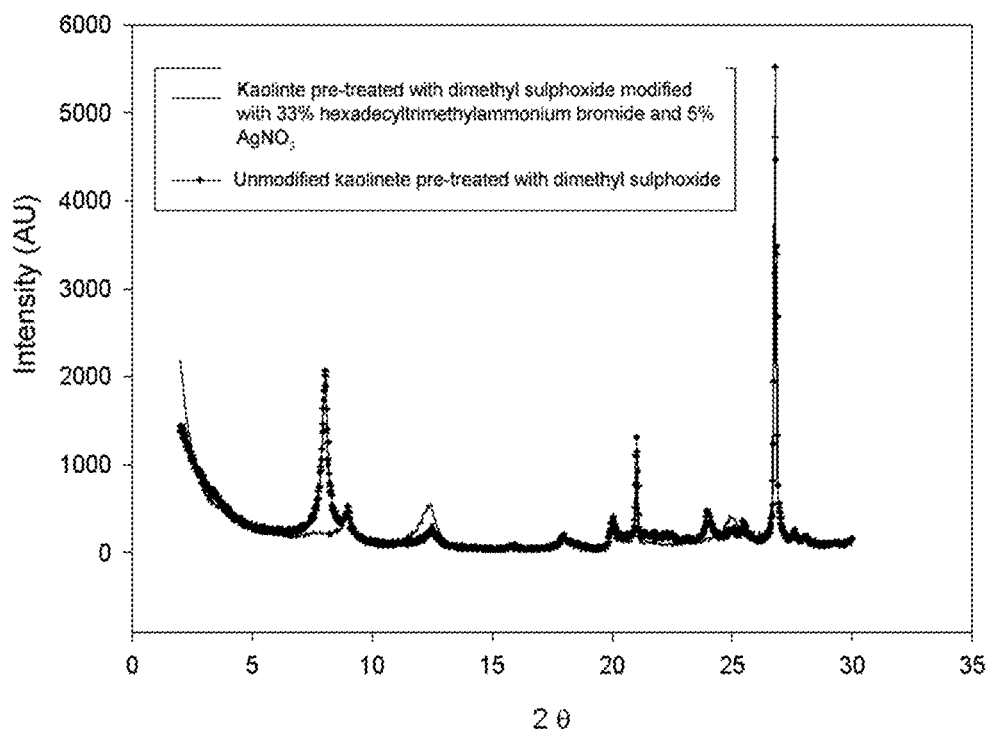
FIG. 3 shows X-ray diffractograms (WAXS) obtained from a sample of kaolinite-type clay (pre-treated with DMSO) modified with hexadecyltrimethylammonium bromide (organic antimicrobial, expander and compatibilising agent) and silver nitrate (temperature-resistant antimicrobial), using UV radiation as the reducing agent by the method described in Example 2, and a sample of the same type of clay without modification (pre-treated with DMSO). This graphic shows how the antimicrobial system is intercalated in the clay and as a result leads to the disappearance of the peak of the natural, pre-treated with DMSO, clay.
Figure 4:
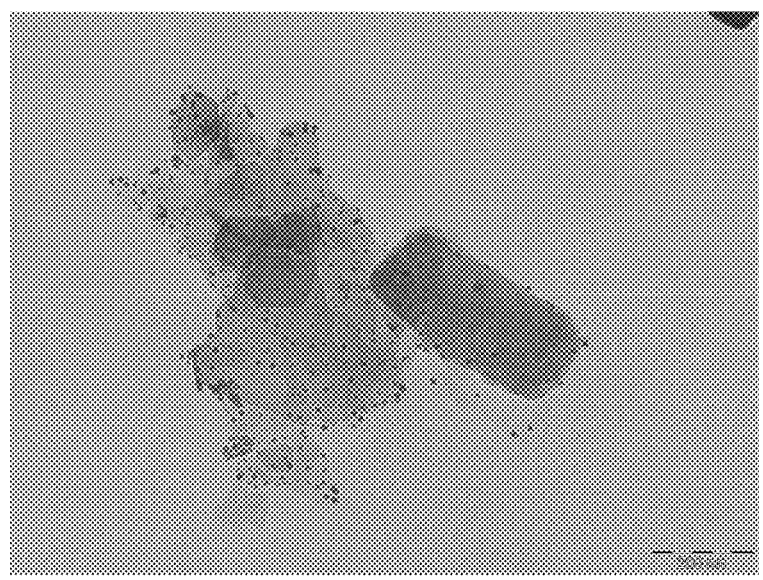
FIG. 4 is an image obtained by transmission electron microscopy (TEM) showing the main and typical morphologies that can be seen in nanoloads obtained according to the present invention. The image shows an aggregate of laminates of kaolinite-type clay (pre-treated with DMSO) modified with hexadecyltrimethylammonium bromide and silver nitrate, using UV radiation as the reducing agent, by the method described in Example 2.

When the clay pre-treated with dimethyl sulphoxide was dry, it was dispersed in water, using 1 g clay per 100 g solvent, and 0.05 g of AgNO3 and 0.33 g hexadecyltrimethylammonium bromide were added. The dispersion was maintained under constant vigorous magnetic stirring and subjected to strong UV radiation of 30 W and 235 nm wavelength. The time for exposure to UV radiation was 24 hours. Then the solid was filtered by suction and dried in a convection oven at 70° C. for 1 hour. The resulting clay was characterised by X-ray diffraction (see FIG. 3) and transmission electronic microscopy (see FIG. 4). The disappearance of the basal peak signal of kaolinite, pre-treated with dimethyl sulphoxide and unmodified with hexadecyltrimethylammonium bromide, in the diffractograms of FIG. 3 (2θ=8.06), indicates that after simultaneous intercalation of hexadecyltrimethylammonium bromide and silver particles, the clay layers are sterically hindered from remaining close together. From the TEM images, it was determined that in this case the silver nanoparticles were between 3 and 24 nm, with an average size of 10 nm; and that these nanoparticles were located on the surface, edges and, presumably, in the interlaminar spaces of the clay. In another study, the antimicrobial ability of this clay with 5% silver nitrate was determined against *Salmonella* spp. A pathogenic microorganism of food origin, *Salmonella* spp. CECT 554, was used, which was obtained from the Spanish Collection of Culture Types (Valencia, Spain). The study conditions were set to use the bacteria in middle exponential phase and with an initial concentration of microorganisms of approximately $10^5$ CFU/mL. The experimental part was carried out using an adaptation of the macro dilution method established for the determination of bactericidal activity of antimicrobial agents approved in 1999 by the National Committee for Clinical Laboratory Standards. According to this method, 100 mg of the clay, which had a final silver nitrate concentration of 5% and hexadecyltrimethylammonium bromide concentration of 33%, was placed in a sterile tube containing 10 mL culture broth Mueller Hinton Broth (MHB). After 5 hours, the tube was inoculated with 0.1 mL of a culture of *Salmonella* spp. in the condition described above. In parallel, two tubes containing a sample without silver (one with a clay of the same type with no modification but pre-treated with DMSO and the other with clay of the same type pre-treated with DMSO and modified with 33% hexadecyltrimethylammonium bromide), and another tube without a sample that acted as a control, were inoculated. After the samples were inoculated, all the tubes were incubated at 37° C. for 24 hours. Next, 0.1 mL of each sample was seeded on Tryptone Soy Agar (TSA) plates. After 24 hours of incubation at 37° C., the viable cells on the plate were counted. Except for the control without a sample and the unmodified clay control pre-treated with dimethyl sulphoxide, a significant reduction in the number of viable cells (>99.9%) was obtained after incubation at 37° C. and 24 hours incubation, both in the control clay pre-treated with DMSO and modified with hexadecyltrimethylammonium bromide and the sample of clay pre-treated with DMSO and modified with hexadecyltrimethylammonium bromide and silver nitrate (see Table 3). These results show that both hexadecyltrimethylammonium bromide and silver nanoparticles intercalated in kaolinite have a strong antimicrobial effect.

TABLE 3

| Sample | Initial CFU/mL | Final CFU/mL |
|---|---|---|
| Control without sample | $7.0 * 10^5$ | $3.8 * 10^9$ |
| Control of kaolinite-type clay pre-treated with dimethyl sulphoxide unmodified with hexadecyltrimethylammonium bromide | $7.0 * 10^5$ | $3.9 * 10^9$ |
| Control of kaolinite-type clay pre-treated with dimethyl sulphoxide and modified with 33% of hexadecyltrimethylammonium bromide | $7.0 * 10^5$ | <1 |
| Kaolinite-type clay pre-treated with dimethyl sulphoxide, modified with 33% hexadecyltrimethylammonium bromide and with 5% AgNO$_3$ | $7.0 * 10^5$ | <1 |

Example 3

Figure 5:
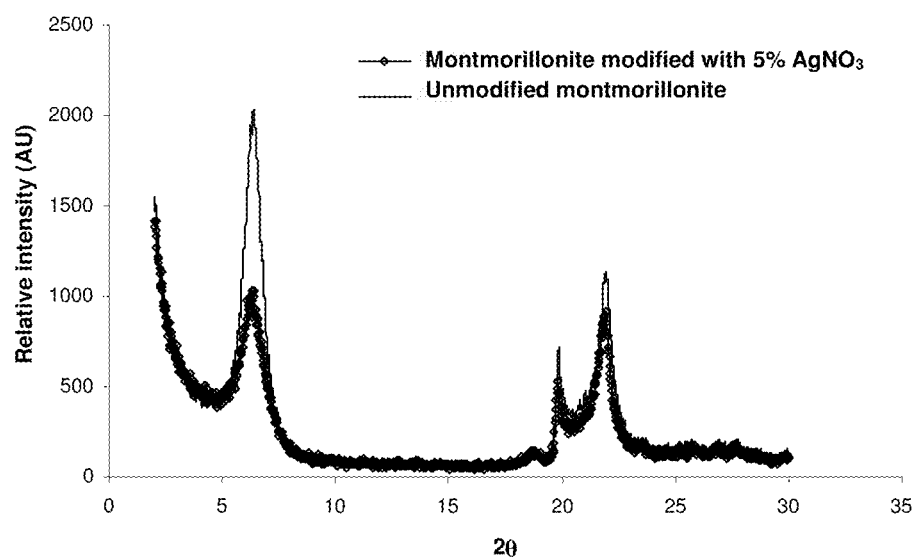
FIG. 5 is an image obtained by transmission electron microscopy (TEM) of an aggregate of layers of montmorillonite-type clay intercalated with silver nitrate, using ethanol as the reducing agent, by the method described in Example 3.

Synthesis and Intercalation of Nanoparticles of Metallic Silver in Unmodified Montmorillonite-Type Clays, Using Ethanol as the Reducing Agent First, the clay was dispersed in ethanol at room temperature, using 1 g of clay per 100 g solvent, and 0.1 g AgNO$_3$ was added to the dispersion. The dispersion was refluxed at 70° C. for 6 hours; then the dispersion was decanted, excess solvent removed and the clay was dried in a convection oven for 1 hour at 70° C. The clay obtained was characterised using X-ray diffraction (see FIG. 5). The diffractograms of FIG. 5 indicate that the basal peak signal (6.38; 2θ) was not displaced after the incorporation of silver nanoparticles in the clay.

In another study, the antimicrobial ability of this clay with 5% silver nitrate was determined against *Salmonella* spp. A pathogenic microorganism of food origin, *Salmonella* spp. CECT 554, was used, which was obtained from the Spanish Collection of Culture Types (Valencia, Spain). The study conditions were set to use the bacteria in middle exponential phase and with an initial concentration of microorganisms of approximately $10^5$ CFU/mL. The experimental part was carried out using an adaptation of the macro dilution method established for the determination of bactericidal activity of antimicrobial agents approved in 1999 by the National Committee for Clinical Laboratory Standards. According to this method, 100 mg of the clay, which had a final silver concentration of 5%, was placed in a sterile tube containing 10 mL culture broth Mueller Hinton Broth (MHB). After 5 hours, the tube was inoculated with 0.1 mL of a culture of *Salmonella* spp. in the condition described above. In parallel, a tube containing a sample without silver and another without a sample were set up for the control. After the samples were inoculated, all the tubes were incubated at 37° C. for 24 hours. Next, 0.1 mL of each sample was seeded on Tryptone Soy Agar (TSA) plates. After 24 hours of incubation at 37° C., the viable cells on the plate were counted. Except for both controls, a significant reduction in the number of viable cells (>99.9%) after incubation at 37° C. for 24 hours was obtained (see Table 4).

TABLE 4

| Sample | Initial CFU/mL | Final CFU/mL |
| --- | --- | --- |
| Control without sample | $7.0 * 10^5$ | $3.8 * 10^9$ |
| Control of unmodified montmorillonite-type clay | $7.0 * 10^5$ | $2.0 * 10^9$ |
| Montmorillonite-type clay modified with 5% of AgNO₃ | $7.0 * 10^5$ | <1 |

Example 4

Synthesis and Intercalation of Nanoparticles of Metallic Silver in Kaolinite-Type Clays Pre-Treated with Dimethyl Sulphoxide, Using UV Radiation as the Reducing Agent First, the kaolinite-type clay was pre-treated with dimethyl sulphoxide to increase interlaminar spacing. For this, 60 g of clay was dispersed in 300 ml of dimethyl sulphoxide, and were stirred magnetically at 65° C. for 24 hours. Next the clay was filtered by suction, washed with methanol and dried in a convection oven at 80° C. for 6 hours.

Figure 6:
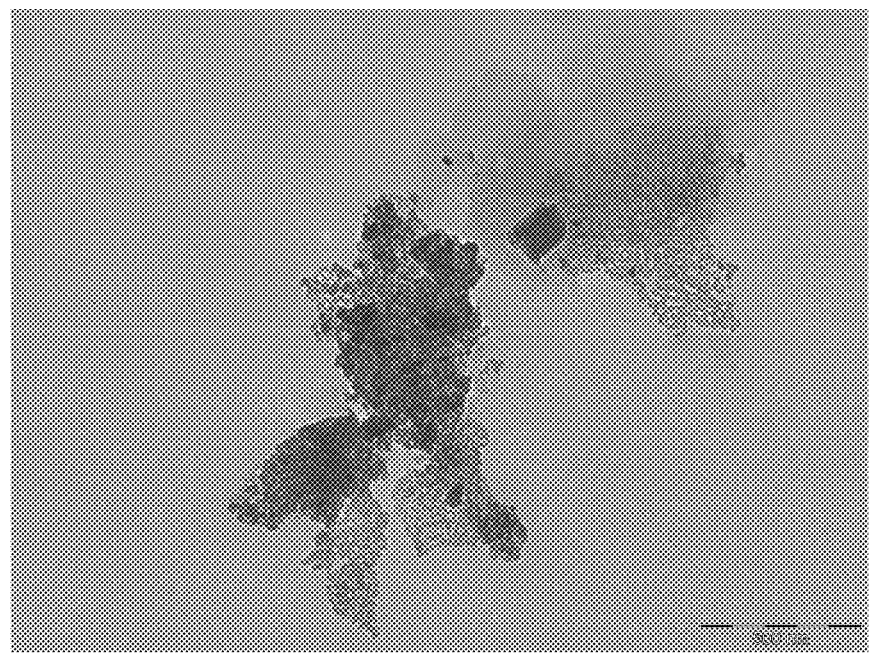
FIG. 6 is an image obtained by transmission electron microscopy (TEM) of an aggregate of layers of kaolinite-type clay (pre-treated with DMSO) intercalated with silver nitrate, using UV radiation as the reducing agent, by the method described in Example 4.

When the clay pre-treated with dimethyl sulphoxide was dry, it was dispersed in water at room temperature, using 1 g clay per 100 g solvent, and 0.05 g of AgNO3 were added. The dispersion was maintained under constant vigorous magnetic stirring and subjected to strong UV radiation of 30 W and 235 nm wavelength. The time of exposure to UV radiation was 24 hours. Then the solid was filtered by suction and dried in a convection oven at 70° C. for 1 hour. The TEM image of FIG. 6 shows an average particle size of silver particles of 15 nm, and these are found on the surfaces and edges of the clay laminates. In another study, the antimicrobial ability of this clay pre-treated with DMSO and modified with 5% silver nitrate was determined against *Salmonella* spp. A pathogenic microorganism of food origin, *Salmonella* spp. CECT 554, was used, which was obtained from the Spanish Collection of Culture Types (Valencia, Spain). The study conditions were set to use the bacteria in middle exponential phase and with an initial concentration of microorganisms of approximately $10^5$ CFU/mL. The experimental part was carried out using an adaptation of the method of macro dilution established for the determination of bactericidal activity of antimicrobial agents approved in 1999 by the National Committee for Clinical Laboratory Standards. According to this method, 100 mg of the clay pre-treated with DMSO, which had a final silver concentration of 5%, was placed in a sterile tube containing 10 mL culture broth Mueller Hinton Broth (MHB). After 5 hours, the tube was inoculated with 0.1 mL of a culture of *Salmonella* spp. in the condition described above. In parallel, a tube containing a sample of the same type of clay pre-treated with dimethyl sulphoxide but without silver and another without a sample was inoculated for the controls. After the samples were inoculated, all the tubes were incubated at 37° C. for 24 hours. Next, 0.1 mL of each sample was seeded on Tryptone Soy Agar (TSA) plates. After 24 hours of incubation at 37° C., the viable cells on the plate were counted. Except for the two controls, a significant reduction in the number of viable cells was obtained (>99.9%) (see Table 5).

TABLE 5

| Sample | Initial CFU/mL | Final CFU/mL |
| --- | --- | --- |
| Control without sample | $7.0 * 10^5$ | $3.8 * 10^9$ |
| Control of kaolinite-type clay pre-treated with dimethyl sulphoxide unmodified with hexadecyltrimethylammonium bromide | $7.0 * 10^5$ | $3.9 * 10^9$ |
| Kaolinite-type clay pre-treated with dimethyl sulphoxide and modified with 5% AgNO₃ | $7.0 * 10^5$ | <1 |

Example 5

Figure 7:
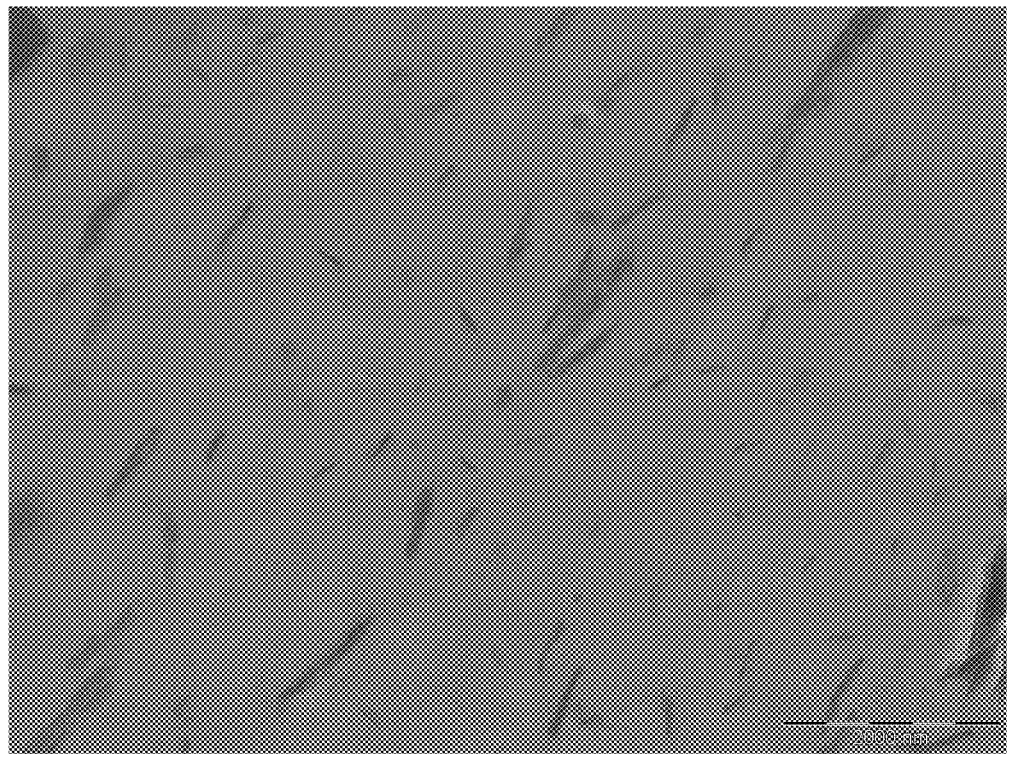
FIG. 7 is an image obtained by transmission electron microscopy (TEM) of a film obtained by casting a nanocomposite of polylactic acid with 10% kaolinite-type clay (pre-treated with DMSO) intercalated with silver nitrate, by the method described in Example 5.
Figure 8:
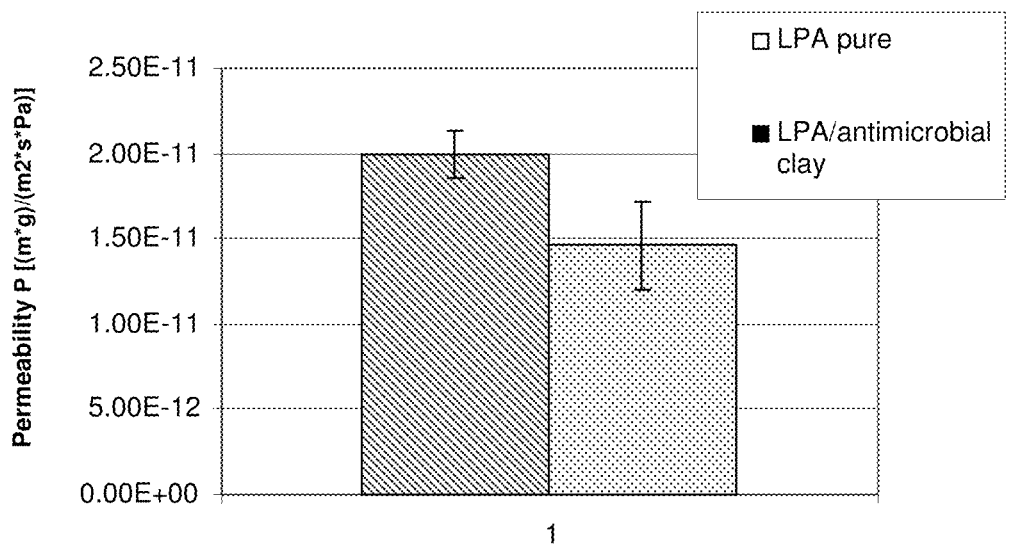
FIG. 8 show the improvement in permeability to water vapour obtained in a film of nanocomposite of polylactic acid with 10% kaolinite-type clay (pre-treated with DMSO) intercalated with silver nitrate compared to a film of pure polylactic acid (Example 5).

Preparation of Films of Polylactic Acid with 10% Kaolinite-Type Clay Pre-Treated with Dimethyl Sulphoxide and Intercalated with Silver Nanoparticles First, dispersion in chloroform was prepared of 10% by weight (of polymer dry weight) of clay pre-treated with dimethyl sulphoxide to which silver nanoparticles had been intercalated by the method of reduction with UV radiation. Next, 5% by weight of polymer (polylactic acid) was added to the dispersion of clay in chloroform. A film of nanocomposite of polylactic acid/silver nanoclay was obtained by evaporation of the solvent at room temperature using the process of casting. These nanocomposites were characterised by studying their morphology by transmission electron microscopy (TEM, see FIG. 7), as well as their water vapour barrier and antimicrobial properties. Additionally, the permeability to water was studied (see FIG. 8) of this polylactic acid film with 10% by weight of clay with microbial properties using the ASTM E96 standard at 25° C. and 75% relative humidity. The addition of antimicrobial clay to the polymeric matrix caused a reduction in permeability of 26.8%, so the composite material shows better water barrier properties than pure polylactic acid.

To evaluate the antimicrobial capacity of PLA films, 600 mg of film were weighed, for both control without clay and for the sample with antimicrobial clay, and placed into 10 mL of sterile culture medium. They were stored at 4° C. for four weeks, prior to inoculation with *Salmonella* spp. Considering that the films contained 10% clay and the clay contained 5% silver nitrate, the final concentration of silver nitrate used was 300 ppm, the minimum bactericidal concentration (in this case, reducing the population to zero) of *Salmonella* being around 100 ppm. The films contain 3 times higher concentration of silver than the bactericidal dose when used in suspension. After four weeks of storage and continuous release, the controls showed an increase in the number of viable cells of three orders of magnitude, whereas in the sample of PLA film with 10% of clay intercalated with silver, the number of viable cells was reduced by three orders of magnitude (see Table 6).

TABLE 6

| Sample | Initial CFU/mL | Final CFU/mL |
| --- | --- | --- |
| Control without sample | $2.0 * 10^5$ | $4.7 * 10^8$ |
| Control of PLA film (without clay) | $2.0 * 10^5$ | $6.6 * 10^8$ |
| PLA film with 10% kaolinite pre-treated with dimethyl sulphoxide and intercalated with silver nanoparticles | $2.0 * 10^5$ | $3.5 * 10^2$ |

Example 6

Preparation of Films of Chitosan with 10% Kaolinite-Type Clay Pre-Treated with Dimethyl Sulphoxide and Intercalated with Silver Nanoparticles First, a solution of 0.9% chitosan in 1% acetic acid at 70° C. was prepared. This solution was filtered and a dispersion of 10% by weight (of polymer dry weight) in water of kaolinite-type clay pre-treated with dimethyl sulphoxide and intercalated with silver nanoparticles was added under vigorous stirring. It was poured into Petri dishes and the solvent left to evaporate at room temperature. A film of nanocomposite of chitosan/silver nanoclay was obtained by process denominated casting. To evaluate the antimicrobial capacity of the chitosan films, different amounts of films were weighed and stored at 4° C. for 12 hours before inoculation with *Salmonella* spp. The weights used were: 25, 50 and 75 mg of film, which were placed in 10 mL tubes of sterile culture medium. The chitosan films contained 10% clay, which in turn contained 5% silver, so the final concentration of silver nitrate used were as follows: 25 mg chitosan film contained 0.125 mg silver nitrate; 50 mg film contained 0.25 mg silver; and 75 mg film contained 0.375 mg silver. The results of Table 7 show that the control chitosan films (without clay) had some antimicrobial activity, because as the weight of the film increased, the number of viable bacteria decreased, the 75 mg of film being sufficient to totally inhibit bacterial growth in the medium under the conditions described. The samples with 10% clay had better capacity for inhibiting growth; with 25 mg of film the number of viable cells reduced by three orders of magnitude and with over 50 mg of film, total inhibition of growth was achieved.

TABLE 7

| Sample | Initial CFU/mL | Final CFU/mL |
| --- | --- | --- |
| Control without sample | $2.0 * 10^5$ | $4.7 * 10^8$ |
| Chitosan control without clay (25 mg) | $2.0 * 10^5$ | $3.5 * 10^6$ |
| Chitosan control without clay (50 mg) | $2.0 * 10^5$ | $2.5 * 10^3$ |
| Chitosan control without clay (75 mg) | $2.0 * 10^5$ | NG |
| Chitosan film with 10% clay pre-treated with dimethyl sulphoxide and intercalated with silver nanoparticles (25 mg sample) | $2.0 * 10^5$ | $1.9 * 10^2$ |
| Chitosan film with 10% clay pre-treated with dimethyl sulphoxide and intercalated with silver nanoparticles (50 mg sample) | $2.0 * 10^5$ | NG |
| Chitosan film with 10% clay pre-treated with dimethyl sulphoxide and intercalated with silver nanoparticles (75 mg sample) | $2.0 * 10^5$ | NG |

Example 7

Evaluation of the Antimicrobial Capacity of PVOH and EVOH Films with 10% Kaolinite-Type Clay Pre-Treated with Dimethyl Sulphoxide and Intercalated with Silver Nanoparticles To 5% solutions of PVOH and EVOH, 10% (by weight of polymer) of kaolinite-type clay pre-treated with dimethyl sulphoxide and intercalated with silver nanoparticles was uniformly incorporated. Next, the respective films were obtained by evaporation of solvent (casting process) and they were stored in a desiccator at 0% relative humidity and room temperature. For the evaluation of antimicrobial capacity, 100 mg of each of the films were placed in 10 mL sterile culture broth and were stored at 4° C. for 72 hours before inoculation with *Salmonella* spp. In parallel, control tubes were prepared without sample and control films of PVOH and EVOH without clays. Additionally, a set of samples and controls under the same conditions were prepared that were processed immediately, in order to study the release of antimicrobial agent from the matrices over time. The results of Table 8 show that the control films without clays allowed the multiplication of the number of viable cells to up to two orders of magnitude, independently of the storage time. Samples of EVOH film with 10% clay intercalated with silver nitrate reduced the number of viable cells 100-fold at the time of inoculation and later 100-fold more after 72 hours incubation. Samples of PVOH films with 10% silver clays reduced the number of viable cells by four orders of magnitude at the time of inoculation of the sample and total inhibition after 72 hours incubation. These results show the bactericide activity of clays intercalated with silver, incorporated into EVOH and PVOH matrices, the antimicrobial effect being more marked in this latter polymer.

TABLE 8

| Sample | Initial CFU/mL | CFU/mL at 0 h | CFU/mL at 72 h |
| --- | --- | --- | --- |
| Control without sample | $1.6 * 10^6$ | $3.9 * 10^8$ | $4.5 * 10^8$ |
| PVOH control | $1.6 * 10^6$ | $1.3 * 10^8$ | $2.7 * 10^8$ |
| EVOH control | $1.6 * 10^6$ | $3.6 * 10^8$ | $1.9 * 10^8$ |
| PVOH + 10% kaolinite pre-treated with dimethyl sulphoxide and intercalated with silver nanoparticles | $1.6 * 10^6$ | $7.3 * 10^2$ | NG |

TABLE 8-continued

| Sample | Initial CFU/mL | CFU/mL at 0 h | CFU/mL at 72 h |
|---|---|---|---|
| EVOH + 10% kaolinite pre-treated with dimethyl sulphoxide and intercalated with silver nanoparticles | $1.6 * 10^6$ | $3.4 * 10^4$ | $2.5 * 10^2$ |

Example 8

Modification of Montmorillonite-Type Clay with 10% w/w of Trans-Resveratrol 99%

Figure 9:
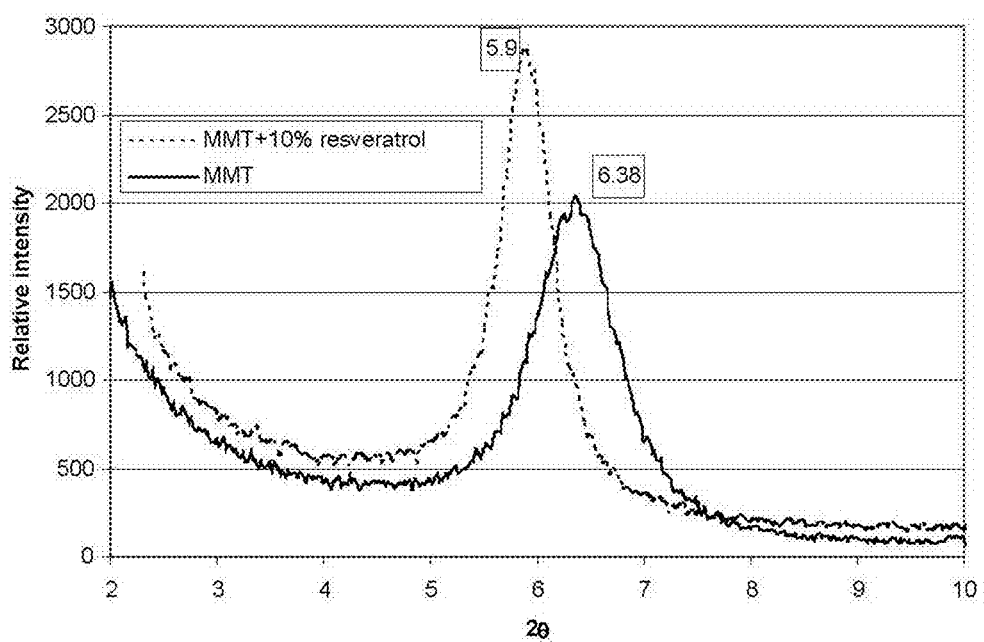
FIG. 9 is an X-ray diffraction spectrum (WAXS) obtained from a sample of montmorillonite-type clay modified with 10% w/w of trans-resveratrol, by the method described in Example 8.
Figure 10:
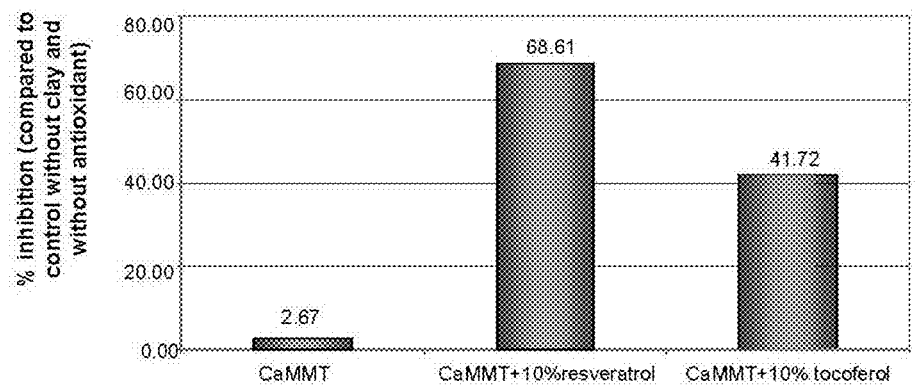
FIG. 10 is a graph of the inhibition of oxidation of linoleic acid in the headspace by the action of montmorillonite-type clays with 10% antioxidants (trans-resveratrol or α-tocopherol), by the methods described in Examples 8 and 9.
Figure 11:
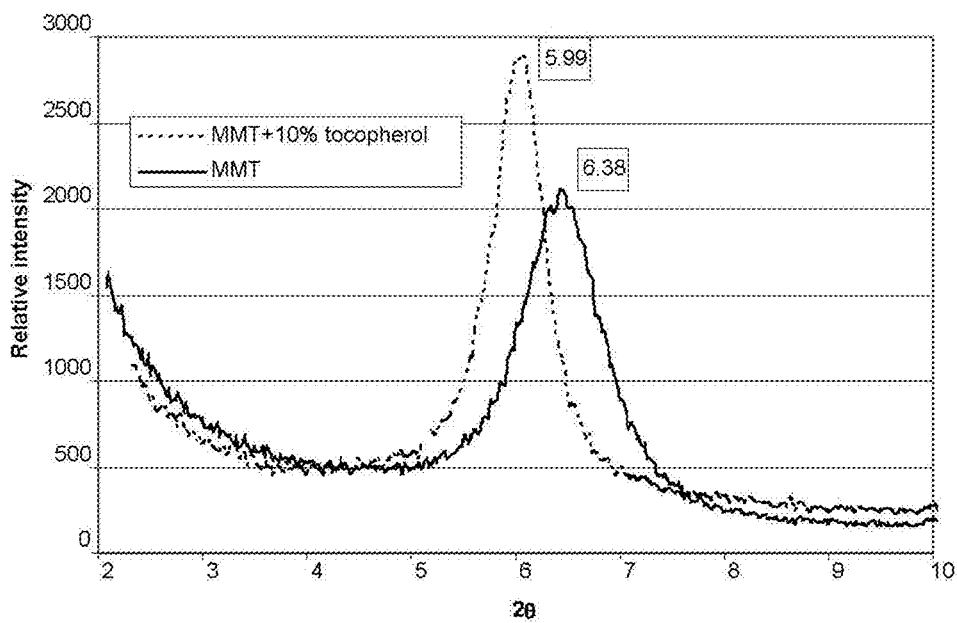
FIG. 11 is an X-ray diffraction spectrum (WAXS) obtained from a sample of montmorillonite-type clay modified with 10% w/w of α-tocopherol, by the method described in Example 9.

First, 2 g of trans-resveratrol was dissolved in a solution of 70% v/v ethanol at 40° C. using magnetic stirring. Next, 20 g of clay was added to the solution of trans-resveratrol. The mixture was maintained under reflux and vigorous stirring at 40° C. for 24 hours. After this time, the resulting clay was filtered by suction and dried in a convection oven at 60° C. for 6 hours. The modified clay was dried and characterised by X-ray diffraction (see FIG. 9). A displacement of the basal peak of 6.38 (2θ) of the unmodified clay to 5.9 (2θ) was observed. According to Bragg's law, this corresponds to an increase in the interlaminar distance of 0.09 nm. Then, the antioxidant effect of the clay modified with 10% trans-resveratrol was determined in the headspace over linoleic acid. For this, 1.6 mmoles of linoleic acid was placed at the bottom of a broad-neck glass flask of 300 mL capacity, distributing the acid around the circumference of the bottom. An amount of modified clay equivalent to 3.2 mmoles of trans-resveratrol were weighed, and placed in a wide-mouth vial at the bottom of the flask containing the acid, avoiding contact with it. Then, the flask was hermetically closed with a plastic bung. At the same time, two other flasks were prepared to act as controls: one contained only the fatty acid and the other contained a vial of unmodified clay in addition to the fatty acid. The three flasks were stored for 48 hours under controlled conditions of 24° C., 75% RH, direct artificial light. After this time, the flasks were opened and 10 mL of 10% w/w trichloracetic acid and 7 mL 20 mM 2-thiobarbituric acid solutions were added. The flasks were stirred and incubated for 30 min at 97° C. Then, the samples were centrifuged, aliquots were taken of the aqueous phase and were diluted 10-fold. The absorbance at 532 nm was measured to determine the concentration of malonaldehyde, a product of the oxidation of linoleic acid. The percentage inhibition of the oxidation of linoleic acid was calculated with respect to the control without clay, obtaining an inhibition of 68.61% (FIG. 10).

Example 9

Modification of Montmorillonite-Type Clay with 10% w/w of α-Tocopherol

First, 2 g of α-tocopherol were dissolved in a solution of 70% v/v ethanol at 40° C. using magnetic stirring. Next, 20 g of clay was added to the solution of α-tocopherol. The mixture was maintained under reflux and vigorous stirring at 40° C. for 24 hours. After this time, the resulting clay was filtered by suction and dried in a convection oven at 60° C. for 6 hours. The modified clay was dried and characterised by X-ray diffraction (see FIG. 3). It was found that the α-tocopherol was introduced between the clay layers because the position of the basal peak changed from 6.38 (2θ) to 5.99 (2θ), corresponding to an opening of 0.09 nm. Then, the antioxidant effect of the clay modified with 10% α-tocopherol was determined in the headspace over linoleic acid. For this, 1.6 mmoles of linoleic acid was placed at the bottom of a broad-neck glass flask of 300 mL capacity, distributing the acid around the circumference of the bottom. An amount of modified clay equivalent to 3.2 mmoles of α-tocopherol were weighed, and placed in a wide-mouth vial at the bottom of the flask containing the acid, avoiding contact with it. Then, the flask was hermetically closed with a plastic bung. At the same time, two other flasks were prepared to act as controls: one contained only the fatty acid and the other contained a vial of unmodified clay in addition to the fatty acid. The three flasks were stored for 48 hours under controlled conditions of 24° C., 75% RH, direct artificial light. After this time, the flasks were opened and 10 mL of 10% w/w trichloracetic acid and 7 mL 20 mM 2-thiobarbituric acid solutions were added. The flasks were stirred and incubated for 30 min at 97° C. Then, the samples were centrifuged, aliquots were taken of the aqueous phase and were diluted 10-fold. The absorbance at 532 nm was measured to determine the concentration of malonaldehyde, a product of the oxidation of linoleic acid. The percentage inhibition of the oxidation of linoleic acid was calculated with respect to the control without clay, obtaining an inhibition of 41.72% (FIG. 10).

Example 10

Figure 12:
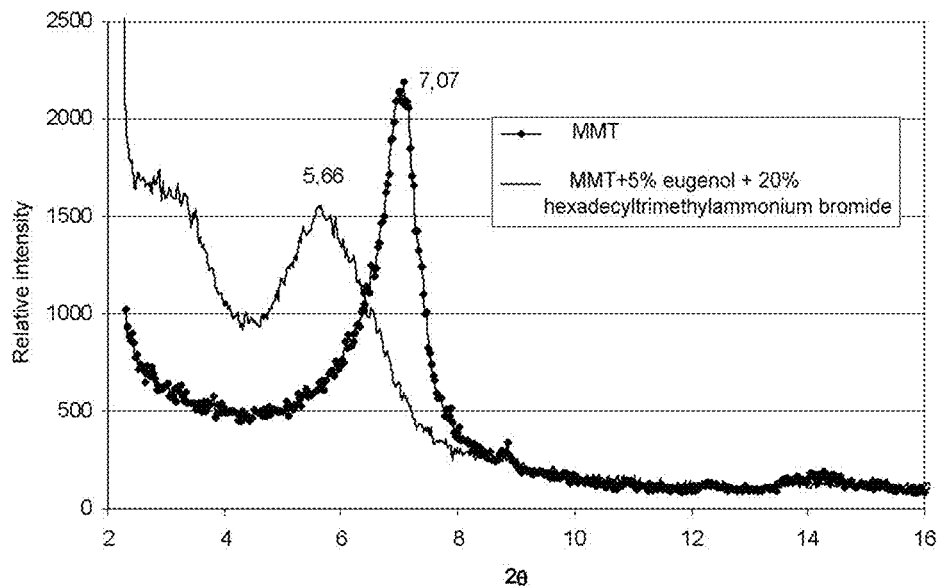
FIG. 12 is an X-ray diffraction spectrum (WAXS) obtained from a sample of montmorillonite-type clay simultaneously modified with 20% w/w of hexadecyltrimethylammonium bromide and 5% eugenol, by the method described in Example 10.

Simultaneous Modification of Montmorillonite-Type Clay with 20% w/w of Hexadecyltrimethylammonium Bromide and 5% w/w Eugenol First, 4 g of hexadecyltrimethylammonium bromide was dissolved in a solution of 20% v/v ethanol at 40° C. using magnetic stirring. Next, 1 g of eugenol and 20 g of clay was added. A high speed homogeniser was used for 10 min to encourage the dispersion of the clay in the solution. The mixture was maintained under reflux and vigorous stirring at 40° C. for 24 hours. After this time, the resulting clay was filtered by suction and dried in a convection oven at 60° C. for 6 hours. The modified clay was dried and characterised by X-ray diffraction (see FIG. 12). The displacement of the basal peak from 7.07 to 5.66 (2θ) indicated an increase in the interlaminar spacing of the order of 0.31 nm, calculated using Bragg's law. This change in spacing is evidence of the entry of the modifying agents into the spaces of the clay.

Example 11

Figure 13:
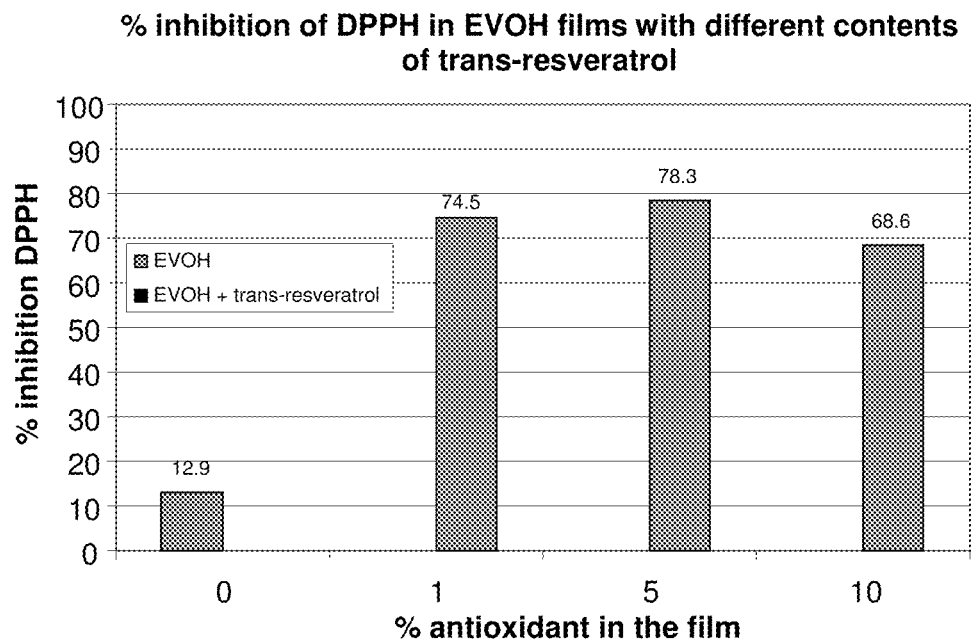
FIG. 13 shows the % inhibition of DPPH in EVOH films with different contents of trans-resveratrol prepared by the method of precipitation, by the process described in Example 11.

Preparation of EVOH32 Films (32% Ethylene) with Different Loads of Trans-Resveratrol by the Precipitation Method EVOH was dissolved with 32% ethylene under reflux at 80° C. in 170 mL of a 50% solution of isopropanol. In another container, the equivalent of 1% w/w of t-resveratrol by total dry weight (polymer+trans-resveratrol) was dissolved in 80 mL of a 50% solution of hot isopropanol at 80° C. When the polymer had dissolved, the hot antioxidant solution was added to the EVOH solution and maintained under magnetic stirring and heating with reflux for 1 hour. The EVOH-antioxidant composite was precipitated by allowing the hot solution to fall in a stream of cold water. The excess water was removed from the precipitated composite, it was cut into small pieces and allowed to dry in a convection oven at 60° C.

for 14 hours. This process enabled the preparation of EVOH composites with 1%, 5% and 10% of trans-resveratrol, using the proportions indicated in Table 9. Then, films were prepared using a press. The samples were transformed into sheets of approx. 100 microns thickness by compression moulding in a hydraulic press at 220° C. and 2 MPa of pressure for 4 minutes. The sheets of sample were slowly cooled inside the press by a flow of water. Next, the antioxidant effect by contact with the EVOH films was determined using the method of colour change of the DPPH (2,2-Diphenyl-1-Picrylhydrazyl) radical. For this, portions of 30 mg of each film were weighed in duplicate and placed in plastic 1.5 mL tubes. To each tube, 1 mL of a stock solution of 0.05 g/L of DPPH in methanol was added. The absorbance at 517 nm of this stock solution was 1.4. In parallel, two control samples without the film were prepared, containing 1 mL of DPPH. The samples and controls were left to incubate in the dark at 24° C. for 24 hours. Then, the absorbance at 517 nm was measured. The results were expressed in % inhibition of DPPH: % inhibition of DPPH=(absorbance control−absorbance sample)/absorbance control. FIG. 13 shows that the films containing trans-resveratrol had an average of 74% antioxidant effect.

TABLE 9

| % antioxidant | EVOH (g) | Antioxidant (g) |
|---|---|---|
| 0 | 25.00 | 0.00 |
| 1 | 24.75 | 0.25 |
| 5 | 23.75 | 1.25 |
| 10 | 22.5 | 2.50 |

Example 12

Figure 14:
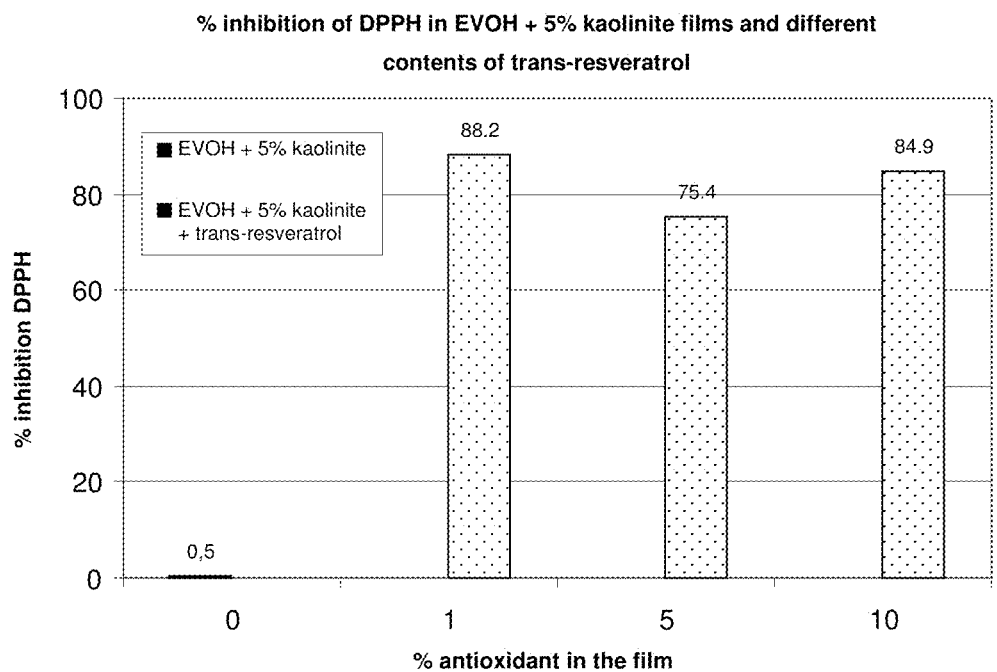
FIG. 14 shows the % inhibition of DPPH in EVOH films with different contents of kaolinite and different contents of resveratrol prepared by the process described in Example 12.

Preparation of EVOH Composites with 5% Kaolinite and with Different Loads of Antioxidant Agents by Extrusion in Liquid EVOH32 and kaolinite were used with a particle size of 10 μm (d90). Water with a conductivity of 150 μS/cm was used. The activation method of the polymer consisted of adding a suspension of kaolinite in water to the melted polymer (extrusion in liquid). The nanoclay content in the resulting composites was calculated by weight loss in thermo gravimetric analysis (approximately 5% by weight). This process enabled preparation of EVOH composites with 1%, 5% and 10% trans-resveratrol. Next, films were prepared using a press. The samples were transformed into sheets of approx. 100 microns thickness by compression moulding in a hydraulic press at 220° C. and 2 MPa of pressure for 4 minutes. The sheets of sample were slowly cooled inside the press by a flow of water. Next, the antioxidant effect by contact with the EVOH films was determined using the method of colour change of the DPPH (2,2-Diphenyl-1-Picrylhydrazyl) radical. For this, portions of 30 mg of each film were weighed in duplicate and placed in plastic 1.5 mL tubes. To each tube, 1 mL of a stock solution of 0.05 g/L of DPPH in methanol was added. The absorbance at 517 nm of this stock solution was 1.4. In parallel; two control samples without the film were prepared, containing 1 mL of DPPH. The samples and controls were left to incubate in the dark at 24° C. for 24 hours. Then, the absorbance at 517 nm was measured. The results were expressed in % inhibition of DPPH: % inhibition of DPPH=(absorbance control−absorbance sample)/absorbance control. FIG. 14 shows that the EVOH films containing 5% of kaolinite and trans-resveratrol of between 1% and 10% had a marked antioxidant effect, because a minimum of 85% inhibition of DPPH was obtained (average 83%). This inhibition power, associated with antioxidant capacity, was maintained in the three concentrations tested. EVOH films containing 5% kaolinite have approx 10% additional inhibition capacity compared to films not containing clay (FIG. 14).

Example 13

Preparation of EVOH Composites with 1% Trans-Resveratrol or 1% α-Tocopherol

Figure 15:
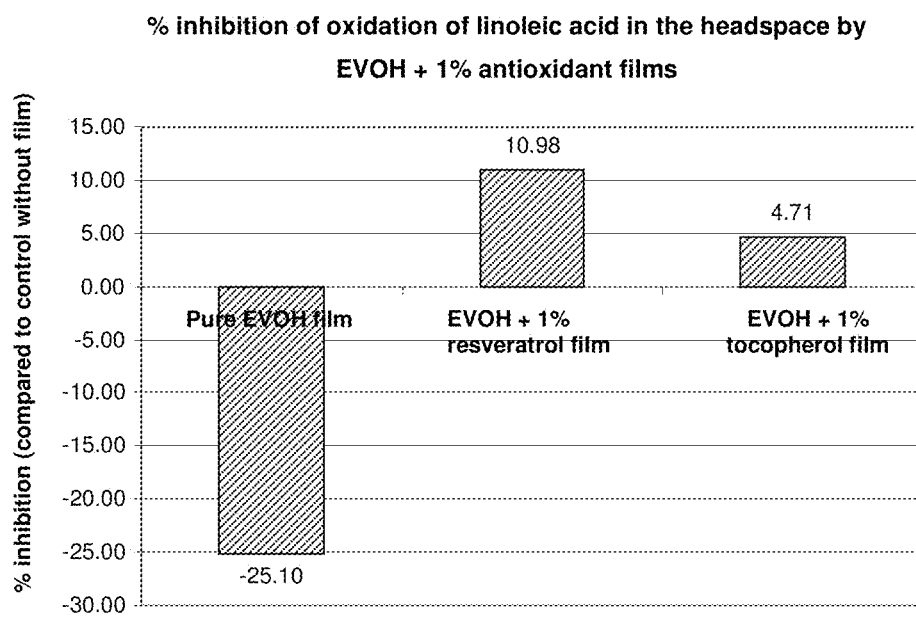
FIG. 15 shows the % inhibition of oxidation of linoleic acid in the headspace by the effect of EVOH+1% antioxidant films, according to the process described in Example 13.

Composites of EVOH32 were prepared using the method of melt mixing for direct aditivation of the polymer with the antioxidant. The three areas of the plastograph were preheated to 220° C. and maintaining a shearing rate of 5 rpm, a total of 16 g of material was introduced into the mixing chamber, alternating polymer and antioxidant. Next, the shearing rate was increased to 100 rpm and mixing continued for 3 min. After this time, the hot material was recovered. Next, once the material had cooled, films were prepared using a press. The samples were transformed into sheets of approx. 100 microns thickness by compression moulding in a hydraulic press at 220° C. and 2 MPa of pressure for 4 minutes. The sheets of sample were slowly cooled inside the press by a flow of water. Next, the antioxidant effect of films of composites of EVOH+1% trans-resveratrol or 1% α-tocopherol was determined in the headspace over linoleic acid. For this, 1.6 mmoles of linoleic acid was placed at the bottom of a broad-neck glass flask of 300 mL capacity, distributing the acid around the circumference of the bottom. Films of approx. 1.2 g in weight were suspended in the headspace of the flasks. Then, the flask was hermetically closed with a plastic bung. At the same time, two other flasks were prepared to act as controls: one contained only the fatty acid and the other contained a film of pure EVOH in addition to the fatty acid. Each sample was prepared in duplicate. The flasks were stored for 10 days under controlled conditions of 24° C., 75% RH and direct artificial light. After this time, the flasks were opened and 10 mL of 10% w/w trichloracetic acid and 7 mL 20 mM 2-thiobarbituric acid solutions were added. The flasks were stirred to aid mixing and incubated for 30 min at 97° C. Then, the samples were centrifuged, aliquots were taken of the aqueous phase and were diluted 10-fold. The absorbance at 532 nm was measured to determine the concentration of malonaldehyde, a product of the oxidation of linoleic acid. The percentage inhibition of the oxidation of linoleic acid was calculated compared to the control without a film. FIG. 15 shows that after 10 days exposure at the conditions indicated, oxidation of linoleic acid was inhibited by 10.98% when it was exposed to a film of EVOH containing 1% resveratrol compared to the target without a film. The film that contained 1% α-tocopherol inhibited the oxidation of linoleic acid by 4.71%. This demonstrates the capture of free radicals from the headspace by resveratrol contained in the film, which demonstrates that the aditivated film has active properties, mainly that film containing trans-resveratrol. The sample that contained only the EVOH film without aditivation degraded by 25% compared to the target without a film.

Example 14

Figure 16:
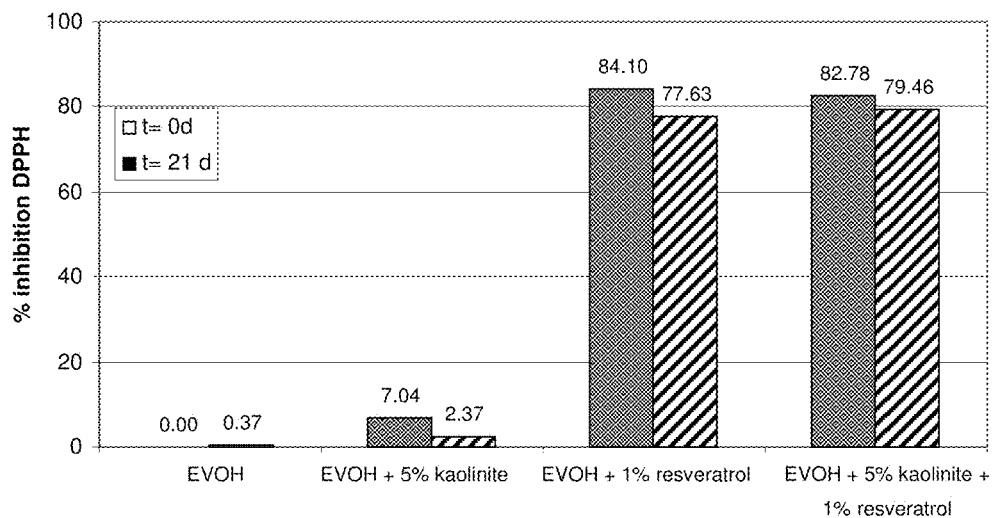
FIG. 16 shows the percentages of inhibition of DPPH radical at time zero and at 21 days of exposure of EVOH films, with and without kaolinite, with 1% antioxidant, exposed to direct artificial light, 24° C. and 40% RH.

Test of the Antioxidant Capacity Over Time of Films of EVOH32 Composites with and Without Kaolinite, with Trans-Resveratrol, Prepared by the Precipitation Method EVOH was dissolved with 32% ethylene under reflux at 80° C. in 170 mL of a 50% solution of isopropanol. In another container, the equivalent of 1% w/w of trans-resveratrol by total dry weight (polymer+trans-resveratrol) was dissolved in 80 mL of a 50% solution of hot isopropanol at 80° C. When the polymer had dissolved, the hot antioxidant solution was added to the EVOH solution and maintained under magnetic stirring and heating with reflux for 1 hour. The EVOH-trans-resveratrol composite was precipitated by allowing the hot solution to fall in a stream of cold water. The excess water was removed from the precipitated composite, it was cut into small pieces and allowed to dry in a convection oven at 60° C. for 14 hours. For the preparation of EVOH composites with 5% kaolinite and 1% trans-resveratrol, EVOH was dissolved with 32% ethylene under reflux at 80° C. in 170 mL of a 50% solution of isopropanol. In a separate container, the equivalent of 1% w/w of trans-resveratrol to total dry weight (polymer+trans-resveratrol) was dissolved in a hot dispersion of kaolinite in 50% v/v isopropanol. Once the polymer had dissolved, the hot dispersion with antioxidant was added to the EVOH solution and maintained under magnetic stirring and heating under reflux for 1 hour. Precipitation was performed in a similar way to that already indicated. Next, films of the EVOH nanocomposites were prepared using a press. The samples were transformed into sheets of approx. 100 microns thickness by compression moulding in a hydraulic press at 220° C. and 2 MPa of pressure for 4 minutes. The sheets of sample were slowly cooled inside the press by a flow of water. Next, the antioxidant effect by contact with the EVOH films was determined using the method of colour change of the DPPH (2,2-Diphenyl-1-Picrylhydrazyl) radical. For this, portions of 30 mg of each film were weighed in duplicate and placed in plastic 1.5 mL tubes. To each tube, 1 mL of a stock solution of 0.05 g/L of DPPH in methanol was added. The absorbance at 517 nm of this stock solution was 1.4. In parallel, two control samples without the film were prepared, containing 1 mL of DPPH. The samples and controls were left to incubate in the dark at 24° C. for 24 hours. Then, the absorbance at 517 nm was measured. The results were expressed in % inhibition of DPPH: % inhibition of DPPH=(absorbance control−absorbance sample)/absorbance control. The films were exposed to direct artificial light at 24° C. and 40% RH and the % inhibition over a time of 21 days was evaluated. FIG. 16 shows the percentages of inhibition of the DPPH radical at time zero and at 21 days of exposure at the test conditions. Table 10 shows that after 21 days of exposure to the test conditions, the loss of antioxidant capacity of the films was 7.7% (maximum). Films of nanocomposite containing kaolinite showed less reduction of antioxidant capacity compared to films not containing kaolinite. This indicates that the clay stabilises the antioxidant incorporated in the polymeric matrix, which means an additional advantage in the use of clays in nanocomposites.

TABLE 10

| EVOH films (casting) | % loss of antioxidant capacity (21 days, artificial light, 24° C., 40% RH) |
|---|---|
| EVOH + 1% resveratrol | 7.70 |
| EVOH + 5% kaolinite + 1% resveratrol | 4.01 |

Example 15

Figure 17:
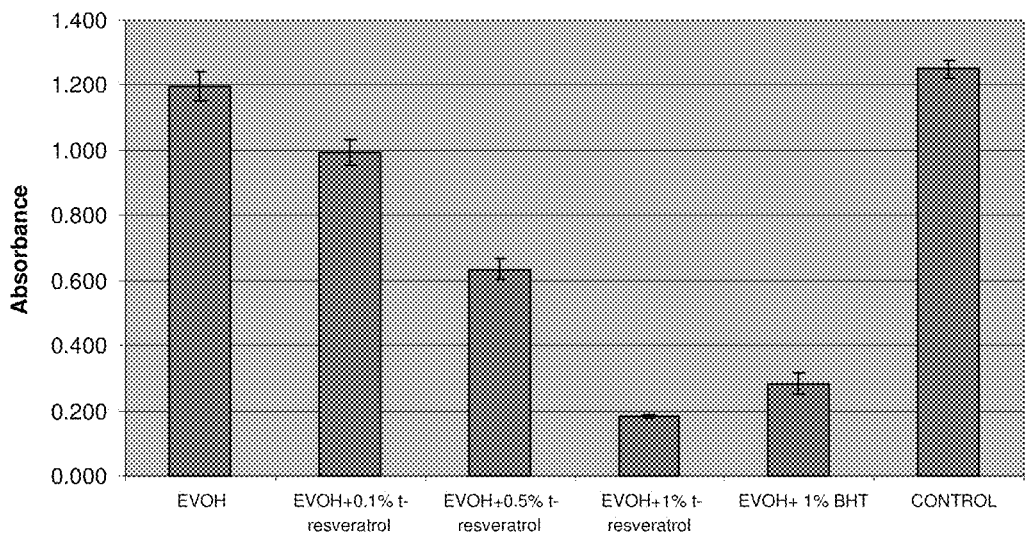
FIG. 17 shows that films of EVOH aditivated with 0.1% to 1% resveratrol in powder have antioxidant ability of between 18.8% and 85.4% (in a DPPH colour change assay), and that EVOH aditivated with 1% resveratrol had higher antioxidant capacity than a film with 1% BHT additive.

Preparation of EVOH Composites with 0.1%-1% Resveratrol by Extrusion, Via Activation in Powder EVOH32 (with 32 molar ethylene) was used as the base polymer and the activation method of the polymer was adding the previously dried antioxidant (97% resveratrol) in powder, to the melted polymer. The process conditions are indicated in Table 11. Similarly, EVOH32 was extruded, being aditivated with 1% butylhydroxytoluene (BHT) to prepare a control material with a commercial antioxidant. Next, films were prepared using a hot plate press. The samples were transformed into sheets of approx. 100 microns thickness by compression moulding in a hydraulic press at 220° C. and 2 MPa of pressure for 4 minutes. The sheets of the samples were cooled with water to room temperature. Next, the antioxidant effect by contact with the resulting EVOH films was determined using the method of colour change of the DPPH (2,2-Diphenyl-1-Picrylhydrazyl) radical. For this, portions of 30 mg of each film were weighed in triplicate and placed in plastic 1.5 mL tubes. To each tube, 1 mL of a stock solution of 0.05 g/L of DPPH in methanol was added. The absorbance at 517 nm of this stock solution was approximately 12. In parallel, three control samples without the film were prepared, containing 1 mL of DPPH. The samples and controls were left to incubate in the dark at 24° C. for 24 hours. Then, the absorbance at 517 nm was measured. The results were expressed in % inhibition of DPPH: % inhibition of DPPH=(absorbance control−absorbance sample)/absorbance control. Table 12 shows the absorbances obtained in each case and the deviations of the means. FIG. 17 shows that films of EVOH aditivated with 0.1% to 1% resveratrol in powder have antioxidant ability of between 18.8% and 85.4% (in a DPPH colour change assay), and that EVOH aditivated with 1% resveratrol had higher antioxidant capacity than a film with 1% BHT additive.

TABLE 11

| Temperature (° C.) | 220.0 |
| Spindle speed (rpm) | 290.0 |
| Rate of production (kg/h) | 9.1 |

TABLE 12

| | Abs 1 | Abs 2 | Abs 3 | Mean Abs | Dev. | Average inhibition (%) |
|---|---|---|---|---|---|---|
| EVOH | 1.197 | 1.243 | 1.151 | 1.197 | 0.046 | 4.189 |
| EVOH + 0.1% t-resveratrol | 1.014 | 0.95 | 1.017 | 0.994 | 0.038 | 18.837 |
| EVOH + 0.5% t-resveratrol | 0.675 | 0.618 | 0.614 | 0.636 | 0.034 | 45.971 |
| EVOH + 1% t-resveratrol | 0.182 | 0.187 | 0.18 | 0.183 | 0.004 | 85.432 |
| EVOH + 1% BTH | 0.246 | 0.303 | 0.3 | 0.283 | 0.032 | 80.309 |
| CONTROL | 1.216 | 1.266 | 1.266 | 1.249 | 0.029 | 2.668 |

Example 16

Preparation of LDPE Composites with 1% t-Resveratrol by Extrusion, Via Aditivation in Liquid Low density polyethylene (LDPE) and 97% resveratrol were used. The aditivation method of the polymer consisted of adding a supersaturated solution of t-resveratrol in isopropanol to the melted polymer mass. The extrusion conditions are shown in Table 13. This process enabled the preparation of LDPE composites with 1% t-resveratrol. Next, films were prepared using a hot plate press. The samples were transformed into sheets of approx. 100 microns thickness by compression moulding in a hydraulic press at 200° C. and 2 MPa of pressure for 4 minutes. The sheets of the samples were slowly cooled by a flow of water to room temperature. Next, the antioxidant effect by contact with the resulting LDPE films was determined using the method of colour change of the DPPH (2,2-Diphenyl-1-Picrylhydrazyl) radical. For this, portions of 30 mg of each film were weighed in triplicate and placed in plastic 1.5 mL tubes. To each tube, 1 mL of a stock solution of 0.05 g/L of DPPH in methanol was added. The absorbance at 517 nm of this stock solution was approximately 1.2. In parallel, three control samples without the film were prepared, containing 1 mL of DPPH. The samples and controls were left to incubate in the dark at 24° C. for 24 hours. Then, the absorbance at 517 nm was measured. The results were expressed in % inhibition of DPPH: % inhibition of DPPH=(absorbance control−absorbance sample)/absorbance control. Table 14 shows the absorbances obtained in each case and the deviations of the means.

Figure 18:
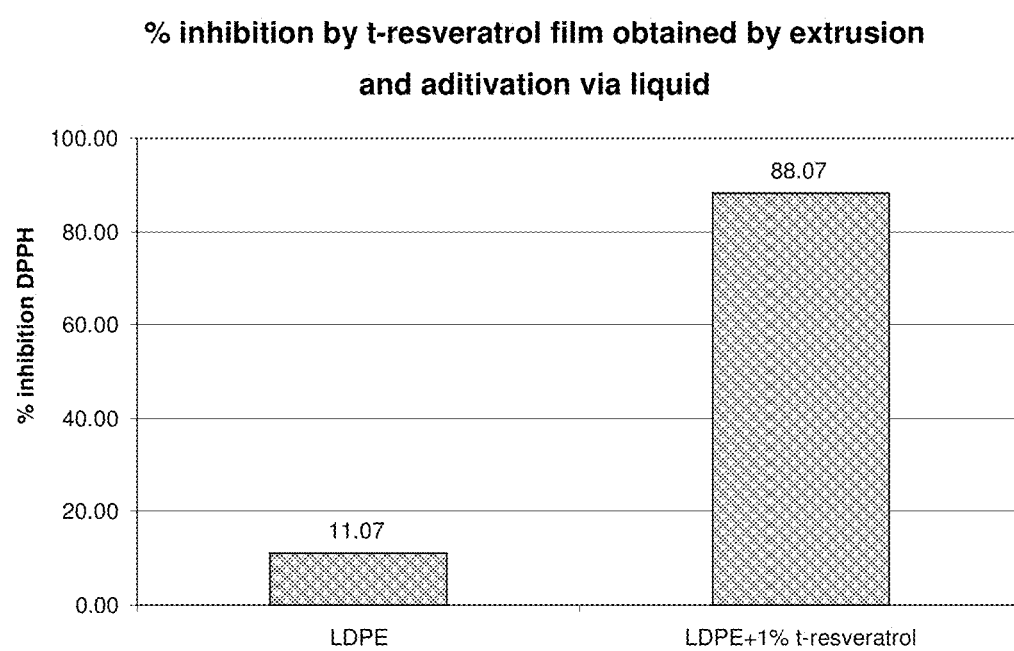
FIG. 18 shows that the LDPE film aditivated with 1% t-resveratrol via liquid has 88% antioxidant ability (in a DPPH colour change assay), clearly better than a LDPE film without aditivation.

FIG. 18 shows that the LDPE film aditivated with 1% t-resveratrol via liquid has 88% antioxidant ability (in a DPPH colour change assay), clearly better than a LDPE film without an aditivation.

TABLE 13

| Temperature (° C.) | 220.0 |
|---|---|
| Spindle speed (rpm) | 300.0 |
| Rate of production (kg/h) | 10.0 |

TABLE 14

|  | Abs 1 | Abs 2 | Abs 3 | Mean Abs | Dev. | Average inhibition (%) |
|---|---|---|---|---|---|---|
| LDPE | 1.111 | 1.15 | 1.111 | 1.124 | 0.023 | 11.073 |
| LDPE + 1% t-resveratrol | 0.149 | 0.14 | 0.165 | 0.151 | 0.013 | 88.074 |
| CONTROL | 1.117 | 1.115 | 1.116 | 1.116 | 0.001 | 10.592 |

Example 17

Preparation of LDPE Composites with a Load of 5% Montmorillonite Modified with 40% Hexadecyltrimethylammonium Bromide and 5% Ammonium-Iron(II) Sulphate by Extrusion Via Powder Aditivation First, the ammonium and iron(II) sulphate was dissolved in ethanol under nitrogen bubbling. Next, the clay modified with 40% hexadecyltrimethylammonium bromide was dispersed in the iron(II) solution using magnetic stirring, maintaining nitrogen bubbling. The proportion of iron(II) salt used was 5% by weight of the unmodified clay, using 20 g of clay per 100 mL solvent. The clay dispersion in metallic solution was refluxed at 70° C. for 6 hours in an inert atmosphere. Next, the dispersion was decanted, excess solvent removed and the clay dried in a vacuum oven at 70° C. for 1 hour. The clay was stored in vacuum in the dark.

For the preparation of the film, low density polyethylene (LDPE) was used as the base polymer, and the method of aditivation of the polymer consisted of adding the montmorillonite clay modified with 40% hexadecyltrimethylammonium bromide (C16) and 5% previously dried ammonium-iron(II) sulphate to the melted polymer. The processing conditions are indicated in Table 15. LDPE without additive was also extruded under the same conditions to use as reference.

Next, films were prepared using a press. The samples were transformed into sheets of approx. 100 microns thickness by compression moulding in a hydraulic press at 200° C. and 2 MPa of pressure for 4 minutes. The sheets of sample were slowly cooled inside the press by a flow of water.

Next, the oxygen sequestration effect of the LDPE films was determined. For this, pieces of films of 4 cm×2 cm were placed in 20 ml vials that contained air at atmospheric conditions and containing a vial with water that generates an activity of one in the headspace. Films of LDPE+5% clay modified with C16 and ammonium-iron(II) sulphate and LDPE films without additive were tested in triplicate. There were also three controls without a film. The oxygen content was determined using an oximeter. At first, the oxygen content in the vials was 20.9% (Table 16). After two days, the percentage of oxygen remained at the same initial value in the control and in the vials containing LDPE film without additive. The oxygen content in vials containing clay modified with C16 salt and iron nanoparticles was reduced to 20.1% (3.8% reduction in oxygen content). The results indicate that the clay containing iron nanoparticles is active when incorporated into a polyolefin matrix by the effect of humidity.

TABLE 15

| Temperature (° C.) | 220.0 |
|---|---|
| Spindle speed (rpm) | 300.0 |
| Rate of production (kg/h) | 10.0 |

TABLE 16

|  | % Oxygen |
|---|---|
| Control without film | 20.9 |
| LDPE film | 20.9 |
| LDPE film + 5% clay modified with 40% C16 salt and iron nanoparticles | 20.1 |

The invention claimed is:

1. Nanocomposite materials comprising the following components:
   a. a plastic or polymeric matrix;
   b. clay having a laminar structure with or without prior organic or inorganic surface modification, wherein said clay comprises montmorillonite, kaolinite, halloysite, or any mixture thereof;
   c. active agent incorporated into the matrix or into the laminar structure of the clay, wherein said active agent is resveratrol.

2. The nanocomposite materials according to claim 1, wherein the plastic or polymeric matrix is selected from the group consisting of polyolefins, polyesters, polyamides, polyimides, polyketones, polyisocyanates, polysulphonates, styrene plastics, phenolic resins, amide resins, ureic resins, melamine resins, polyester resins, epoxide resins, polycarbonates, polyvinylpyrrolidines, epoxy resins, polyacrylates, rubbers and gums, polyurethanes, silicones, aramids, polybutadiene, polyisoprenes, polyacrylonitriles, PVDF, PVA, PVOH, EVOH, PVC, PVDC, proteins, polysaccharides, lipids and biopolyesters, and mixtures thereof.

3. The nanocomposite materials according to claim 1, wherein the clay is in a proportion from 0.01% to 95%.

4. The nanocomposite materials according to claim 1, wherein the clay is modified with organic compounds selected from the group consisting of quaternary ammonium salts, esters of polyethylene glycol with mono carboxylic aliphatic acids (C6-C22) and their ammonium and sodium sulphates, perfluorooctanoic acid and its ammonium salt, copolymers of N-methylacryloyloxyethyl-N,N-dimethyl-N-carboxymethylammonium chloride, bis(2-hydroxyethyl)-2-hydroypropyl-3-(dodecyloxy)methylammonium chloride and combinations thereof.

5. Process for obtaining nanocomposite materials according to claim 1, comprising the following stages:
   a. reduction of the size of the clay by mechanical action;
   b. classification of the particles obtained in the previous stage by filtration via dry or wet methods;
   c. alternatively, removal of organic material, crystalline oxides and hard particles not subject to modification until a laminar structure of the clay is obtained;
   d. obtaining laminar fines either in liquid suspension or as powder;
   e. pre-treatment of the laminar structure by an expander precursor;
   f. intercalation of resveratrol into the laminar structure, wherein the resveratrol is in aqueous base or in a polar solvent;
   g. addition of the product obtained in stage (f) to a plastic or polymeric matrix.

6. Process for obtaining nanocomposite materials according to claim 5, wherein the reduction of size of the clay is carried out until the particle sizes are below 30 microns in D90.

7. Process according to claim 5, wherein the filtration is carried out until the particle size of the clay is from 0.1 to 100 microns.

8. Process according to claim 5, wherein the removal of organic matter is performed by decantation, collection of supernatant or chemical reaction with oxidising substances.

9. Process according to claim 5, wherein the removal of crystalline oxides and hard particles not subject to modification is carried out by centrifugation and/or gravimetry in solution by turbo-driers.

10. Process according to claim 5, wherein the precursors are further comprises expanders and/or compatibilisers.

11. Process according to claim 5, wherein after the pre-treatment stage of the laminar structure by the precursor, the laminar structure is dried.

12. Process according to claim 5, wherein after pre-treatment of the laminar structures by the precursor, the laminar structure is intercalated with polymeric, biopolymeric, active or bioactive modifiers or mixes thereof, optionally followed by washing and/or drying.

13. Process according to claim 5, wherein in the stage of addition to the plastic or ceramic matrix, incorporation of active and bioactive substances selected from the group consisting of metals, metallic or antimicrobial inorganic salts, antimicrobial organic products, oxygen sequestration agents, antioxidant compounds, and combinations thereof is carried out.

14. Process according to claim 5 wherein, a physical or chemical treatment is carried out to totally or partially charge the oxidation state of the metallic centre intercalated in the matrix.

15. Process according to claim 12, wherein the modifiers are selected from the group consisting of inorganic modifiers, organic modifiers, materials derived from biomass and/or biodegradables, salts, and antimicrobial compounds.

16. The nanocomposite materials according to claim 1, wherein the clay is in a proportion from 0.01 to 80%.

17. The nanocomposite materials according to claim 1, wherein the clay is in a proportion from 0.01 to 10%.

18. The nanocomposite materials according to claim 1, wherein the matrix is selected from the group consisting of polyolefins, polyesters, polyamides, styrene plastics, polyester resins, polyacrylates, polyurethanes, silicones, polyacrylonitriles, PVA, PVOH, EVOH, biopolyesters, and mixtures thereof.

19. The nanocomposite materials according to claim 1, wherein the clay further comprises quaternary ammonium salts incorporated into the laminar structure.

20. The nanocomposite materials according to claim 19, wherein the quaternary ammonium salt is hexadecyltrimethylammonium bromide.

21. Process for obtaining nanocomposite materials according to claim 1, comprising the following stages:
   a. reduction of the size of the clay by mechanical action;
   b. classification of the particles obtained in the previous stage by filtration via dry or wet methods;
   c. alternatively, removal of organic material, crystalline oxides and hard particles not subject to modification until a laminar structure of the clay is obtained;
   d. obtaining laminar fines either in liquid suspension or as powder;
   e. addition of the product obtained in stage (d) and resveratrol in solid or liquid state, either via liquid dispersed in polar or apolar solvent or via solid to a plastic or polymeric matrix.

\* \* \* \* \*